US010301687B2

(12) United States Patent
Zhang et al.

(10) Patent No.: US 10,301,687 B2
(45) Date of Patent: May 28, 2019

(54) *SIDT 1* GENE CONTROLLING DETERMINATE GROWTH HABIT IN SESAME AND SNP MOLECULAR MARKER THEREOF

(71) Applicant: Henan Sesame Research Center, Henan Academy of Agricultural Sciences, Zhengzhou (CN)

(72) Inventors: Haiyang Zhang, Zhengzhou (CN); Hongmei Miao, Zhengzhou (CN); Chun Li, Zhengzhou (CN); Libin Wei, Zhengzhou (CN); Yinghui Duan, Zhengzhou (CN); Fangfang Xu, Zhengzhou (CN); Huili Wang, Zhengzhou (CN)

(73) Assignee: HENAN SESAME RESEARCH CENTER, HENAN ACADEMY OF AGRICULTURAL SCIENCES, Zhengzhou (CN)

( * ) Notice: Subject to any disclaimer, the term of this patent is extended or adjusted under 35 U.S.C. 154(b) by 76 days.

(21) Appl. No.: 15/499,863

(22) Filed: Apr. 27, 2017

(65) Prior Publication Data

US 2017/0233831 A1 Aug. 17, 2017

Related U.S. Application Data

(63) Continuation-in-part of application No. PCT/CN2015/099095, filed on Dec. 28, 2015.

(30) Foreign Application Priority Data

Dec. 3, 2015 (CN) .......................... 2015 1 0876016

(51) Int. Cl.

| | |
|---|---|
| ***C12Q 1/68*** | (2018.01) |
| ***C07H 21/02*** | (2006.01) |
| ***C12Q 1/6895*** | (2018.01) |
| ***C07K 14/415*** | (2006.01) |
| ***A01H 1/04*** | (2006.01) |
| ***A01H 5/10*** | (2018.01) |

(52) U.S. Cl.

CPC ............. *C12Q 1/6895* (2013.01); *A01H 1/04* (2013.01); *A01H 5/10* (2013.01); *C07K 14/415* (2013.01); *C12Q 2600/13* (2013.01); *C12Q 2600/156* (2013.01)

(58) Field of Classification Search

None

See application file for complete search history.

(56) References Cited

PUBLICATIONS

Zhang et al Sci. Rep. 6:31556; doi: 10.1038/srep31556, pp. 1-13 and Supplemental material, pp. 1-12. Published Aug. 16, 2016.*

NCBI Database Accession No. KU240042, Jul. 16, 2016, available via URL: <ncbi.nlm.nih.gov/nuccore/1043186749?sat=4&satkey=167521988>.*

* cited by examiner

*Primary Examiner* — Carla J Myers

(74) *Attorney, Agent, or Firm* — Matthias Scholl P.C.; Matthias Scholl

(57) ABSTRACT

A Sidt1 gene controlling a determinate growth habit of sesame, the gene having a length of 1809 bp and including four exons and three introns. The Sidt1 gene is located on the fourth chromosome of sesame and in an 18.0-19.2 cM interval of the eighth linkage group on an SNP genetic map of sesame. The DNA sequence of the Sidt1 gene is represented by SEQ ID NO. 1. A cDNA sequence of the Sidt1 gene has a length of 531 bp and encodes 176 amino acids, and the cDNA sequence is represented by SEQ ID NO. 2. An SNP molecular marker Sidt27-1 of the Sidt1 gene has a length of 92 bp and is located at a base sequence from 378 to 469 of the Sidt1 gene, and a DNA sequence of the SNP molecular marker Sidt27-1 is represented by SEQ ID NO. 3.

5 Claims, 14 Drawing Sheets

Specification includes a Sequence Listing.

SEQUENCE LISTING

<160> NUMBER OF SEQ ID NOS: 49

<210> SEQ ID NO 1
<211> LENGTH: 1809
<212> TYPE: DNA
<213> ORGANISM: Sesamum indicum

<400> SEQUENCE: 1

```
atggcaaaaa tgtcatcgga ccccccttgtg atcggtaggg tggtcggaga cgttgtcgat     60
catttctcct ccaccgtcaa aatgtcagtc acttacaact ccaacaagca tgtctacaat    120
ggccatgagc tcttcccttc cacagtcacc tctaaaccta gggttgaggt ccatggtggt    180
gatatgagat catttttcac cctggtaaca ataattttac taatgatttt ttacacaccc    240
cactacttct ttcttctaat ttctgctgat attttttttgg gagtttgtgt aaattaaagt    300
agtacgtgca aatatttcgt gggttttcag taataatttc ctcgtttata tatatgtttg    360
atcagatcat gacagaccct gatgttcctg gtcctaatga tccatatctg agggagcacc    420
tgcactggta tgctttcatt tttaactgct taagacctga ttgatttaat aaactagtat    480
tcttcaaaaa actagagttt tggaatgatc aacacccttt tctcatccaa gagggtaatc    540
aaccacaaca cactttttag ggttttttct tttagttttt ttaaaaaatt atggtagaaa    600
ccgttattga aatagtctat tggaggggtc gatcatatat atatatatat atgtatgtgt    660
tgggtggact ataaaattga agagaaatta attttagaaa aaggagatta aaacgtaatt    720
ctaaatgcaa acaaatttaa atactattgc attacaattt taagatttct ctgcaaaaaa    780
ctaagctcct aggaaagttc gttcacttta aggtacaaga tgtattataa aattttttttg    840
gtgataatac atgagattcg taagtttaga gtgatggtct acactacatg tgatgtaagg    900
tccacaaatc ccgcatcata tgtgtcagac gcactacgaa aaacccttgt ttcatcctat    960
gaaaaaagta ggtttcatcg agtcacttcc aactaaatct ctgtccaagt gatgatccat   1020
gaaaatgttg tttgtcgtgt cgactatcct tcatttcatt attcctatgg aaaattaccc   1080
tttaaaaata tactcttgcc tggttccacg tcttctattt caacatcgta ttatctgatt   1140
gttgaatagt gataatttga ctgtcgaaat tacataaagc acaatattaa aatagaataa   1200
ctaaatctgt atcggattct caattgttta ccctagttaa aaaaatattg cttatatatg   1260
tggcttgaca aatgtactta taattaatta atcacataaa catttgacaa acaatgagcc   1320
ctctttcaaa aacacctgac aagtgcagtt aactaatgaa ttacgttgtt ttttatttta   1380
catatatgta ctaaatctac tgacaaacat aagttgattt gacgaactca caggatagtc   1440
acagatatcc ctggcaccac agattcctca ttcggtatga ataaagatca tatatactcc   1500
atttaattaa tatcttattt aaatctttgt tttcacatta attaattaat tttcttgttt   1560
acatgtaatt atcaatgtac tgcaggaaaa gaagtagtga gctacgagat gccgaggcca   1620
aacataggaa tacacaggtt tgcatttgtg ctgttcaagc agaagaagag acaattagga   1680
tgcgtgaggg caccagcttg tagggatgga ttcaatacca ggaattttgc ccaggaaaat   1740
gagttaggtc tccctgttgc tgctgtttac ttcaattgcc agagagagac tgctgctaga   1800
aggcgctag                                                           1809
```

<210> SEQ ID NO 2
<211> LENGTH: 531
<212> TYPE: DNA
<213> ORGANISM: Sesamum indicum

<400> SEQUENCE: 2

-continued

```
atggcaaaaa tgtcatcgga ccccccttgtg atcggtaggg tggtcggaga cgttgtcgat     60

catttctcct ccaccgtcaa aatgtcagtc acttacaact ccaacaagca tgtctacaat    120

ggccatgagc tcttcccttc cacagtcacc tctaaaccta gggttgaggt ccatggtggt    180

gatatgagat catttttcac cctgatcatg acagaccctg atgttcctgg tcctaatgat    240

ccatatctga gggagcacct gcactggata gtcacagata tccctggcac cacagattcc    300

tcattcggaa aagaagtagt gagctacgag atgccgaggc caaacatagg aatacacagg    360

tttgcatttg tgctgttcaa gcagaagaag agacaattag gatgcgtgag ggcaccagct    420

tgtagggatg gattcaatac caggaatttt gcccaggaaa atgagttagg tctccctgtt    480

gctgctgttt acttcaattg ccagagagag actgctgcta gaaggcgcta g             531


<210> SEQ ID NO 3
<211> LENGTH: 92
<212> TYPE: DNA
<213> ORGANISM: Sesamum indicum

<400> SEQUENCE: 3

cctgatgttc ctggtcctaa tgatccatat ctgagggagc acctgcactg gtatgctttc     60

atttttaact gcttaagacc tgattgattt aa                                   92


<210> SEQ ID NO 4
<211> LENGTH: 20
<212> TYPE: DNA
<213> ORGANISM: Artificial Sequence
<220> FEATURE:
<223> OTHER INFORMATION: Forward primer HSDt01-1F

<400> SEQUENCE: 4

cctgatgttc ctggtccgaa                                                 20


<210> SEQ ID NO 5
<211> LENGTH: 25
<212> TYPE: DNA
<213> ORGANISM: Artificial Sequence
<220> FEATURE:
<223> OTHER INFORMATION: Forward primer HSDt01-2F

<400> SEQUENCE: 5

ctattcctga tgttcctggt ccgag                                           25


<210> SEQ ID NO 6
<211> LENGTH: 24
<212> TYPE: DNA
<213> ORGANISM: Artificial Sequence
<220> FEATURE:
<223> OTHER INFORMATION: Reverse primer HSDt01- R

<400> SEQUENCE: 6

taaatcaatc aggtcttaag cagt                                            24


<210> SEQ ID NO 7
<211> LENGTH: 22
<212> TYPE: DNA
<213> ORGANISM: Artificial Sequence
<220> FEATURE:
<223> OTHER INFORMATION: Forward primer Dt1 Primer F

<400> SEQUENCE: 7

atggcaaaaa tgtcatcgga cc                                              22
```

-continued

<210> SEQ ID NO 8
<211> LENGTH: 22
<212> TYPE: DNA
<213> ORGANISM: Artificial Sequence
<220> FEATURE:
<223> OTHER INFORMATION: Reverse primer Dt1 Primer R

<400> SEQUENCE: 8
ctagcgcctt ctagcagcag tc 22

<210> SEQ ID NO 9
<211> LENGTH: 531
<212> TYPE: DNA
<213> ORGANISM: Sesamum indicum

<400> SEQUENCE: 9
atggcaaaaa tgtcatcgga ccccccttgtg atcggtaggg tggtcggaga cgttgtcgat 60
catttctcct ccaccgtcaa aatgtcagtc acttacaact ccaacaagca tgtctacaat 120
ggccatgagc tcttcccttc cacagtcacc tctaaaccta gggttgaggt ccatggtggt 180
gatatgagat catttttcac cctgatcatg acagaccctg atgttcctgg tcctagtgat 240
ccatatctga gggagcacct gcactggata gtcacagata tccctggcac cacagattcc 300
tcattcggaa aagaagtagt gagctacgag atgccgaggc caaacatagg aatacacagg 360
tttgcatttg tgctgttcaa gcagaagaag agacaattag gatgcgtgag ggcaccagct 420
tgtagggatg gattcaatac caggaatttt gcccaggaaa atgagttagg tctccctgtt 480
gctgctgttt acttcaattg ccagagagag actgctgcta gaaggcgcta g 531

<210> SEQ ID NO 10
<211> LENGTH: 176
<212> TYPE: PRT
<213> ORGANISM: Sesamum indicum

<400> SEQUENCE: 10

Met Ala Lys Met Ser Ser Asp Pro Leu Val Ile Gly Arg Val Val Gly
1 5 10 15

Asp Val Val Asp His Phe Ser Ser Thr Val Lys Met Ser Val Thr Tyr
20 25 30

Asn Ser Asn Lys His Val Tyr Asn Gly His Glu Leu Phe Pro Ser Thr
35 40 45

Val Thr Ser Lys Pro Arg Val Glu Val His Gly Gly Asp Met Arg Ser
50 55 60

Phe Phe Thr Leu Ile Met Thr Asp Pro Asp Val Pro Gly Pro Ser Asp
65 70 75 80

Pro Tyr Leu Arg Glu His Leu His Trp Ile Val Thr Asp Ile Pro Gly
85 90 95

Thr Thr Asp Ser Ser Phe Gly Lys Glu Val Val Ser Tyr Glu Met Pro
100 105 110

Arg Pro Asn Ile Gly Ile His Arg Phe Ala Phe Val Leu Phe Lys Gln
115 120 125

Lys Lys Arg Gln Leu Gly Cys Val Arg Ala Pro Ala Cys Arg Asp Gly
130 135 140

Phe Asn Thr Arg Asn Phe Ala Gln Glu Asn Glu Leu Gly Leu Pro Val
145 150 155 160

Ala Ala Val Tyr Phe Asn Cys Gln Arg Glu Thr Ala Ala Arg Arg Arg
165 170 175

<210> SEQ ID NO 11
<211> LENGTH: 176
<212> TYPE: PRT
<213> ORGANISM: Sesamum indicum

<400> SEQUENCE: 11

```
Met Ala Lys Met Ser Ser Asp Pro Leu Val Ile Gly Arg Val Val Gly
1               5                   10                  15

Asp Val Val Asp His Phe Ser Ser Thr Val Lys Met Ser Val Thr Tyr
            20                  25                  30

Asn Ser Asn Lys His Val Tyr Asn Gly His Glu Leu Phe Pro Ser Thr
        35                  40                  45

Val Thr Ser Lys Pro Arg Val Glu Val His Gly Gly Asp Met Arg Ser
    50                  55                  60

Phe Phe Thr Leu Ile Met Thr Asp Pro Asp Val Pro Gly Pro Asn Asp
65                  70                  75                  80

Pro Tyr Leu Arg Glu His Leu His Trp Ile Val Thr Asp Ile Pro Gly
                85                  90                  95

Thr Thr Asp Ser Ser Phe Gly Lys Glu Val Val Ser Tyr Glu Met Pro
            100                 105                 110

Arg Pro Asn Ile Gly Ile His Arg Phe Ala Phe Val Leu Phe Lys Gln
        115                 120                 125

Lys Lys Arg Gln Leu Gly Cys Val Arg Ala Pro Ala Cys Arg Asp Gly
    130                 135                 140

Phe Asn Thr Arg Asn Phe Ala Gln Glu Asn Glu Leu Gly Leu Pro Val
145                 150                 155                 160

Ala Ala Val Tyr Phe Asn Cys Gln Arg Glu Thr Ala Ala Arg Arg Arg
                165                 170                 175
```

<210> SEQ ID NO 12
<211> LENGTH: 19
<212> TYPE: DNA
<213> ORGANISM: Artificial Sequence
<220> FEATURE:
<223> OTHER INFORMATION: Forward primer HSDt02-F

<400> SEQUENCE: 12
ttggggtttg gagtcttgg 19

<210> SEQ ID NO 13
<211> LENGTH: 25
<212> TYPE: DNA
<213> ORGANISM: Artificial Sequence
<220> FEATURE:
<223> OTHER INFORMATION: Reverse primer HSDt02-1R

<400> SEQUENCE: 13
aatgattgat gtctgtgtgt gtcta 25

<210> SEQ ID NO 14
<211> LENGTH: 30
<212> TYPE: DNA
<213> ORGANISM: Artificial Sequence
<220> FEATURE:
<223> OTHER INFORMATION: Reverse primer HSDt02-2R

<400> SEQUENCE: 14
tattaaatga ttgatgtctg tgtgtgtctt 30

<210> SEQ ID NO 15

<211> LENGTH: 25
<212> TYPE: DNA
<213> ORGANISM: Artificial Sequence
<220> FEATURE:
<223> OTHER INFORMATION: Forward primer HSDt03-F

<400> SEQUENCE: 15
attactccat agtcgaggaa gaaac 25

<210> SEQ ID NO 16
<211> LENGTH: 25
<212> TYPE: DNA
<213> ORGANISM: Artificial Sequence
<220> FEATURE:
<223> OTHER INFORMATION: Reverse primer HSDt03-1R

<400> SEQUENCE: 16
acaccttaat agaaaaacaa aatca 25

<210> SEQ ID NO 17
<211> LENGTH: 30
<212> TYPE: DNA
<213> ORGANISM: Artificial Sequence
<220> FEATURE:
<223> OTHER INFORMATION: Reverse primer HSDt03-2R

<400> SEQUENCE: 17
tatatacacc ttaatagaaa aacaaaatcg 30

<210> SEQ ID NO 18
<211> LENGTH: 25
<212> TYPE: DNA
<213> ORGANISM: Artificial Sequence
<220> FEATURE:
<223> OTHER INFORMATION: Forward primer HSDt04-1F

<400> SEQUENCE: 18
acaattaata catgtatatg tgccc 25

<210> SEQ ID NO 19
<211> LENGTH: 30
<212> TYPE: DNA
<213> ORGANISM: Artificial Sequence
<220> FEATURE:
<223> OTHER INFORMATION: Forward primer HSDt04-2F

<400> SEQUENCE: 19
tatatacaat taatacatgt atatgtggcg 30

<210> SEQ ID NO 20
<211> LENGTH: 25
<212> TYPE: DNA
<213> ORGANISM: Artificial Sequence
<220> FEATURE:
<223> OTHER INFORMATION: Reverse primer HSDt04-R

<400> SEQUENCE: 20
ctctctccct ctctcataca caaat 25

<210> SEQ ID NO 21
<211> LENGTH: 22
<212> TYPE: DNA
<213> ORGANISM: Artificial Sequence
<220> FEATURE:
<223> OTHER INFORMATION: Forward primer HSDt05-F

<400> SEQUENCE: 21
aagttttgaa ccaacgtaaa ca 22

<210> SEQ ID NO 22
<211> LENGTH: 25
<212> TYPE: DNA
<213> ORGANISM: Artificial Sequence
<220> FEATURE:
<223> OTHER INFORMATION: Reverse primer HSDt05-1R

<400> SEQUENCE: 22
attgatcagt aaagattatc atggt 25

<210> SEQ ID NO 23
<211> LENGTH: 30
<212> TYPE: DNA
<213> ORGANISM: Artificial Sequence
<220> FEATURE:
<223> OTHER INFORMATION: Reverse primer HSDt05-2R

<400> SEQUENCE: 23
atataattga tcagtaaaga ttatcatggc 30

<210> SEQ ID NO 24
<211> LENGTH: 20
<212> TYPE: DNA
<213> ORGANISM: Artificial Sequence
<220> FEATURE:
<223> OTHER INFORMATION: Forward primer HSDt06-1F

<400> SEQUENCE: 24
tgctcaacct ccatttggcg 20

<210> SEQ ID NO 25
<211> LENGTH: 25
<212> TYPE: DNA
<213> ORGANISM: Artificial Sequence
<220> FEATURE:
<223> OTHER INFORMATION: Forward primer HSDt06-2F

<400> SEQUENCE: 25
tatattgctc aacctccatt tggca 25

<210> SEQ ID NO 26
<211> LENGTH: 23
<212> TYPE: DNA
<213> ORGANISM: Artificial Sequence
<220> FEATURE:
<223> OTHER INFORMATION: Reverse primer HSDt06-R

<400> SEQUENCE: 26
caacacgtgc tatcatctga atc 23

<210> SEQ ID NO 27
<211> LENGTH: 24
<212> TYPE: DNA
<213> ORGANISM: Artificial Sequence
<220> FEATURE:
<223> OTHER INFORMATION: Forward primer HSDt07-1F

<400> SEQUENCE: 27
cgcaggtttt attctgatat actg 24

<210> SEQ ID NO 28
<211> LENGTH: 29
<212> TYPE: DNA

<213> ORGANISM: Artificial Sequence
<220> FEATURE:
<223> OTHER INFORMATION: Forward primer HSDt07-2F

<400> SEQUENCE: 28
atatacgcag gttttattct gatatacta 29

<210> SEQ ID NO 29
<211> LENGTH: 25
<212> TYPE: DNA
<213> ORGANISM: Artificial Sequence
<220> FEATURE:
<223> OTHER INFORMATION: Reverse primer HSDt07-R

<400> SEQUENCE: 29
actctcgtac ttctctcttg aaccc 25

<210> SEQ ID NO 30
<211> LENGTH: 25
<212> TYPE: DNA
<213> ORGANISM: Artificial Sequence
<220> FEATURE:
<223> OTHER INFORMATION: Forward primer HSDt08-1F

<400> SEQUENCE: 30
aaataacaaa ggtgtaaatc attcc 25

<210> SEQ ID NO 31
<211> LENGTH: 30
<212> TYPE: DNA
<213> ORGANISM: Artificial Sequence
<220> FEATURE:
<223> OTHER INFORMATION: Forward primer HSDt08-2F

<400> SEQUENCE: 31
aatataaata acaaaggtgt aaatcattct 30

<210> SEQ ID NO 32
<211> LENGTH: 25
<212> TYPE: DNA
<213> ORGANISM: Artificial Sequence
<220> FEATURE:
<223> OTHER INFORMATION: Reverse primer HSDt08-R

<400> SEQUENCE: 32
agtagtcgcc ataaactata actca 25

<210> SEQ ID NO 33
<211> LENGTH: 25
<212> TYPE: DNA
<213> ORGANISM: Artificial Sequence
<220> FEATURE:
<223> OTHER INFORMATION: Forward primer HSDt09-F

<400> SEQUENCE: 33
cacaattttc tcatttcact cggaa 25

<210> SEQ ID NO 34
<211> LENGTH: 25
<212> TYPE: DNA
<213> ORGANISM: Artificial Sequence
<220> FEATURE:
<223> OTHER INFORMATION: Reverse primer HSDt09-1R

<400> SEQUENCE: 34
taggatgtgg gtttgttcta tacat 25

-continued

<210> SEQ ID NO 35
<211> LENGTH: 30
<212> TYPE: DNA
<213> ORGANISM: Artificial Sequence
<220> FEATURE:
<223> OTHER INFORMATION: Reverse primer HSDt09-2R

<400> SEQUENCE: 35
tatattagga tgtgggtttg ttctatacag 30

<210> SEQ ID NO 36
<211> LENGTH: 24
<212> TYPE: DNA
<213> ORGANISM: Artificial Sequence
<220> FEATURE:
<223> OTHER INFORMATION: Forward primer HSDt10-F

<400> SEQUENCE: 36
aatcaattgg taaggatggt atca 24

<210> SEQ ID NO 37
<211> LENGTH: 25
<212> TYPE: DNA
<213> ORGANISM: Artificial Sequence
<220> FEATURE:
<223> OTHER INFORMATION: Reverse primer HSDt10-R

<400> SEQUENCE: 37
ttattcgtca cttacagatt atcca 25

<210> SEQ ID NO 38
<211> LENGTH: 26
<212> TYPE: DNA
<213> ORGANISM: Artificial Sequence
<220> FEATURE:
<223> OTHER INFORMATION: Forward primer HSDt11-F

<400> SEQUENCE: 38
gcatttagaa ttacgtttta atctcc 26

<210> SEQ ID NO 39
<211> LENGTH: 25
<212> TYPE: DNA
<213> ORGANISM: Artificial Sequence
<220> FEATURE:
<223> OTHER INFORMATION: Reverse primer HSDt11-R

<400> SEQUENCE: 39
aaccgttatt gaaatagtct attgg 25

<210> SEQ ID NO 40
<211> LENGTH: 25
<212> TYPE: DNA
<213> ORGANISM: Artificial Sequence
<220> FEATURE:
<223> OTHER INFORMATION: Forward primer HSDt12-F

<400> SEQUENCE: 40
tattattgcc gttcttattg ttttt 25

<210> SEQ ID NO 41
<211> LENGTH: 25
<212> TYPE: DNA
<213> ORGANISM: Artificial Sequence
<220> FEATURE:

-continued

<223> OTHER INFORMATION: Reverse primer HSDt12-R

<400> SEQUENCE: 41
cgtcattttt ttggttatat ttcta 25

<210> SEQ ID NO 42
<211> LENGTH: 25
<212> TYPE: DNA
<213> ORGANISM: Artificial Sequence
<220> FEATURE:
<223> OTHER INFORMATION: Forward primer HSDt13-F

<400> SEQUENCE: 42
tggataagca tacacacacc aacat 25

<210> SEQ ID NO 43
<211> LENGTH: 21
<212> TYPE: DNA
<213> ORGANISM: Artificial Sequence
<220> FEATURE:
<223> OTHER INFORMATION: Reverse primer HSDt13-R

<400> SEQUENCE: 43
aacttgctgc agagggactc g 21

<210> SEQ ID NO 44
<211> LENGTH: 21
<212> TYPE: DNA
<213> ORGANISM: Artificial Sequence
<220> FEATURE:
<223> OTHER INFORMATION: Forward primer HSDt14-F

<400> SEQUENCE: 44
gccgcaattt aatttctttc a 21

<210> SEQ ID NO 45
<211> LENGTH: 25
<212> TYPE: DNA
<213> ORGANISM: Artificial Sequence
<220> FEATURE:
<223> OTHER INFORMATION: Reverse primer HSDt14-R

<400> SEQUENCE: 45
gactagagac tccccacact tagat 25

<210> SEQ ID NO 46
<211> LENGTH: 24
<212> TYPE: DNA
<213> ORGANISM: Artificial Sequence
<220> FEATURE:
<223> OTHER INFORMATION: Forward primer HSDt15-F

<400> SEQUENCE: 46
tttttagccg tattccgaga ctat 24

<210> SEQ ID NO 47
<211> LENGTH: 25
<212> TYPE: DNA
<213> ORGANISM: Artificial Sequence
<220> FEATURE:
<223> OTHER INFORMATION: Reverse primer HSDt15-R

<400> SEQUENCE: 47
atggctctat ctaccaaaat ctaat 25

-continued

```
<210> SEQ ID NO 48
<211> LENGTH: 21
<212> TYPE: DNA
<213> ORGANISM: Artificial Sequence
<220> FEATURE:
<223> OTHER INFORMATION: Forward primer of Dt-Gs

<400> SEQUENCE: 48

gagccctctt tcaaaaacac c                                              21


<210> SEQ ID NO 49
<211> LENGTH: 20
<212> TYPE: DNA
<213> ORGANISM: Artificial Sequence
<220> FEATURE:
<223> OTHER INFORMATION: Reverse primer of Dt-Gs

<400> SEQUENCE: 49

agcagcaaca gggagaccta                                                20
```

*SIDT 1* GENE CONTROLLING DETERMINATE GROWTH HABIT IN SESAME AND SNP MOLECULAR MARKER THEREOF

CROSS-REFERENCE TO RELATED APPLICATIONS

This application is a continuation-in-part of International Patent Application No. PCT/CN2015/099095 with an international filing date of Dec. 28, 2015, designating the United States, now pending, and further claims foreign priority benefits to Chinese Patent Application No. 201510876016.3 filed Dec. 3, 2015. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to a Sidt1 gene for controlling the determinate growth habit trait in sesame and a single nucleotide polymorphism (SNP) molecular marker Sidt27-1 thereof.

Description of the Related Art

Sesame (*Sesamum indicum* L.) is an indeterminate crop and has a long flowering stage of between 25 and 35 days. Its indeterminate growth habit results in nonsynchronous ripening of capsules, which increases the difficulty for mechanical harvesting, and adversely affects the yield and quality of sesame products.

Conventional determinate genotypes of sesame have limited number of capsule nodes and low yield, thus not being suitable for direct production.

SUMMARY OF THE INVENTION

In view of the above-described problems, one objective of the invention is to provide a Sidt1 gene for controlling the determinate growth habit in sesame and a cDNA sequence of Sidt1 gene. Another objective of the invention is to provide an SNP molecular marker of the Sidt1 gene for facilitating screening and breeding of new sesame varieties.

To achieve the above objectives, in accordance with one embodiment of the invention, there is provided a Sidt1 gene for controlling the determinate growth habit trait in sesame. The Sidt1 gene has a length of 1809 bp and comprises four exons and three introns. The Sidt1 gene is located on the fourth chromosome of sesame and in an 18.0-19.2 cM interval of the eighth linkage group on an SNP genetic map of sesame. An interpretation ratio of the Sidt1 gene to the determinate phenotype is 100% (Vg/Vp). A DNA sequence of the Sidt1 gene is represented by SEQ ID NO. 1.

In accordance with another embodiment of the invention, there is provided a cDNA sequence of the Sidt1 gene. The cDNA sequence has a length of 531 bp and encodes 176 amino acids; and the cDNA sequence is represented by SEQ ID NO. 2.

It should be noted that the cDNA sequence of the Sidt1 gene is the same as the gene sequence of the normal plant (dt0) except that the nucleotide of the 236th site in the cDNA sequence is mutated from "G" into "A". When the "G" is mutated into "A", the 79th amino acid in the encoded protein sequence is correspondingly mutated from serine (S) into asparagine (N), and the inflorescence of the plant is changed from the indeterminate type (dt0 type) into the determinate type (dt1 type).

In accordance with still another embodiment of the invention, there is provided an SNP molecular marker Sidt27-1 of the Sidt1 gene, wherein the SNP molecular marker Sidt27-1 has a length of 92 bp and is located at a base sequence from 378 to 469 of the Sidt1 gene. A DNA sequence of the SNP molecular marker Sidt27-1 is represented by

```
SEQ ID NO. 3:
CCTGATGTTCCTGGTCCTAATGATCCATATCTGAGGGAGCACCTGCACTG
GTATGCTTTCATTTTTAACTGCTTAAGACCTGATTGATTTAA.
```

In accordance with still another embodiment of the invention, there is provided a method for identifying the Sidt1 gene using the SNP molecular marker Sidt27-1. The method comprises:

1) extracting a genome DNA of a germplasm material of sesame to be identified;

2) using an extracted DNA of 1) as a template for PCR amplification by using the following primers:

```
a forward primer HSDt01-1F represented by SEQ ID
NO. 4:
5' CCTGATGTTCCTGGTCCGAA 3';

a forward primer HSDt01-2F represented by SEQ ID
NO. 5:
5' CTATTCCTGATGTTCCTGGTCCGAG 3';
and

a reverse primer HSDt01-R represented by SEQ ID
NO. 6:
5' TAAATCAATCAGGTCTTAAGCAGT 3';
```

performing gel electrophoresis on PCR amplified products, and determining whether the genome DNA of the germplasm material of sesame to be identified comprises the SNP molecular marker Sidt27-1 according to the following rules:

if the genome DNA only comprises the SNP molecular marker Sidt27-1, when the primer pair HSDt01-1F and HSDt01-R are adopted for PCR amplification and a product having a band size of 92 bp is amplified, the germplasm material of sesame is determined to belong to a dt1 type having the determinate inflorescence and is adapted to cultivate sesame varieties having a determinate inflorescence;

if the genome DNA is in the absence of the SNP molecular marker Sidt27-1, when the primer pair HSDt01-2F and HSDt01-R are adopted for PCR amplification and a product having a band size of 97 bp is amplified, the germplasm material of the sesame is determined to belong to a dt0 type having an indeterminate growth phenotype and is adapted to cultivate sesame varieties having an indeterminate inflorescence; and if both the product having the band size of 92 bp and the product having the band size of 97 bp are amplified, the germplasm material of the sesame is determined to belong to a hybrid type having the indeterminate habit; and the determinate inflorescence materials are obtained after trait segregation of progeny of the hybrid type.

In a class of this embodiment, for further determining whether the germplasm material to be identified comprises the Sidt1 gene, the extracted DNA of 1) is used as the template for PCR amplification using the following primer pair:

```
a forward primer Dt1 Primer F represented by SEQ
ID NO. 7:
5'-ATGGCAAAAATGTCATCGGACC-3';
and

a reverse primer Dt1 Primer R represented by SEQ
ID NO. 8:
5'-CTAGCGCCTTCTAGCAGCAGTC-3'.
```

The PCR amplified products are sequenced and aligned with the Sidt1 gene, and if the PCR amplified products match with the Sidt1 gene, the germplasm material to be identified is determined to belong to the determinate phenotype. The Sidt1 gene is represented by SEQ ID NO. 1.

In 2012, Yuzhi DS899 (single stem, 15-20 capsule nodes) and 08TP092 (branched, 2-3 capsule nodes) were crossed in order to study the mutation trait of $F_1$ generation and $F_2$ generation. It was indicated from results that $F_1$ progeny all presented the determinate growth habit with 3-5 capsule nodes, and $F_2$ progeny all presented determinate growth habit with 3-15 capsule nodes. Combined with other research results, it was considered that in the determinate varieties Yuzhi DS899 and 08TP092, the determinate inflorescence trait is controlled by a same gene, while the inflorescence traits present certain differences. Then, genes for controlling the determinate growth habit in the two germplasm genotypes are nominated as Sidt1 (originated from Yuzhi DS899) and Sidt2 (originated from 08TP092). Correspondingly, mutants of Yuzhi DS899 and 08TP092 are defined as a dt1 type and a dt2 type, respectively, and a normal variety with indeterminate growth habit is defined as a dt0 type.

It was known from subsequent study results that the difference between the determinate germplasm materials of the dt1 type and the dt2 type is that mutations occur in different base fragments in the sequence of the SiDt gene. Since 2013, $F_2$ populations constructed by Yuzhi DS899 (dt1 type)×JS012 (dt0 type) was utilized in reference to population mapping and genome fine mapping of sesame using whole-genome resequencing techniques, the Sidt1 gene of Yuzhi DS899 was successfully cloned, and was denominated as Sitfl in genome annotation of sesame. Finally, the mutant gene locus of the determinate growth habit trait of sesame was identified, which was the fundamental of studying the mechanism for the inflorescence development regulation and selection of the new varieties with dt1 type and benefited the development of the molecular-assisted selection techniques in sesame.

Based on the gene sequence, the molecular marker of the acquired Sidt1 gene controlling the determinate growth habit of sesame was developed and applied, which provides technical support for facilitating the genetic basis of important traits and breeding new varieties in sesame.

Innovative points of the invention are as follows:

1) Genome resequencing and construction of the SNP molecular genetic map for sesame are performed using the mutant Yuzhi DS899 with the determinate growth habit, the Sidt1 gene controlling the determinate growth habit of sesame is cloned and the SNP marker Sidt27-1 is developed. In the meanwhile, a PCR amplification method for identifying whether a germplasm material contains the target gene and the target marker locus is also provided. The method is adaptable to preliminary identification of the inflorescence development type of various sesame varieties to be tested quickly and conveniently, thus providing reference for new variety breeding.

2) Sequences of the Sidt1 gene controlling the determinate growth habit in sesame and the SNP marker Sidt27-1 are specific, and the identification results are stable and reliable. The gene controlling the determinate growth habit of concern possesses great influence on the yield, seed quality, and the production of sesame and has great importance on the study of flower development mechanism of plants such as sesame and new variety breeding adapted to mechanical production in sesame.

3) The method for identifying the Sidt1 gene controlling the determinate growth habit in sesame and the SNP marker Sidt27-1 provided in the invention adopts mature molecular biological techniques, and the identification results are stable, which improves the working efficiency of new variety breeding.

Advantages of the Sidt1 gene, the cDNA of the Sidt1 gene, the SNP molecular marker Sidt27-1, and the method for identifying the Sidt1 gene using the SNP molecular marker Sidt27-1 according to embodiments of the invention are summarized as follows:

1) The Sidt1 gene controlling the determinate growth habit of sesame is discovered for the first time.

2) The SNP marker Sidt27-1 of the Sidt1 gene controlling the determinate growth habit of sesame is developed and therefore provides the genetic information for analyzing the flower development mechanism of plants such as the sesame.

3) The SNP molecular marker Sidt27-1 provided in the invention is an important molecular maker for the molecular assisted breeding technique for sesame and provides a fast detecting method for screening of the new sesame varieties with the determinate growth habit trait.

BRIEF DESCRIPTION OF THE DRAWINGS

The invention is described herein below with reference to the accompanying drawings, in which.

DETAILED DESCRIPTION OF THE EMBODIMENTS

Figure 1:
FIG. 1 are pictures of plantlets of Yuzhi DS899 (dt1 type, determinate florescence, right) and parent Yuzhi 11 (dt0 type, indeterminate florescence, left) in accordance with one embodiment of the invention.
Figure 2A:
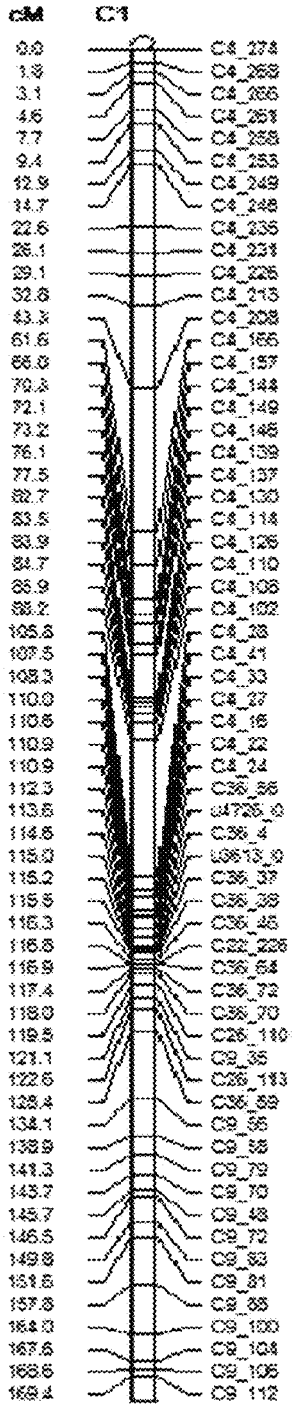
FIGS. 2A-2M are linkage groups of an ultra-dense SNP genetic map for sesame constructed using an $F_2$ population in accordance with one embodiment of the invention.
Figure 2B:
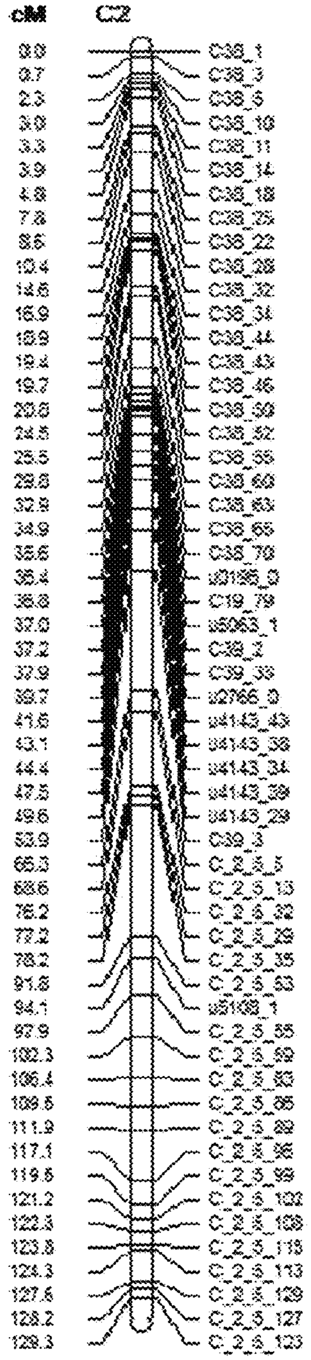
Figure 2C:
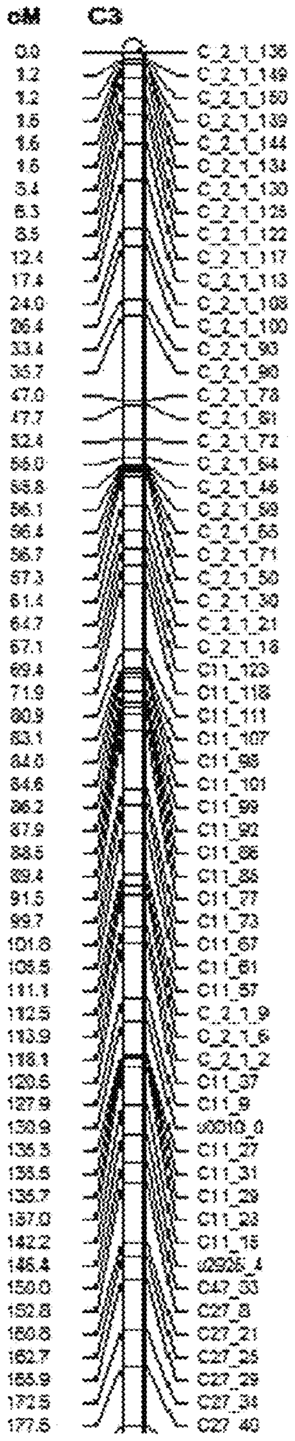
Figure 2D:
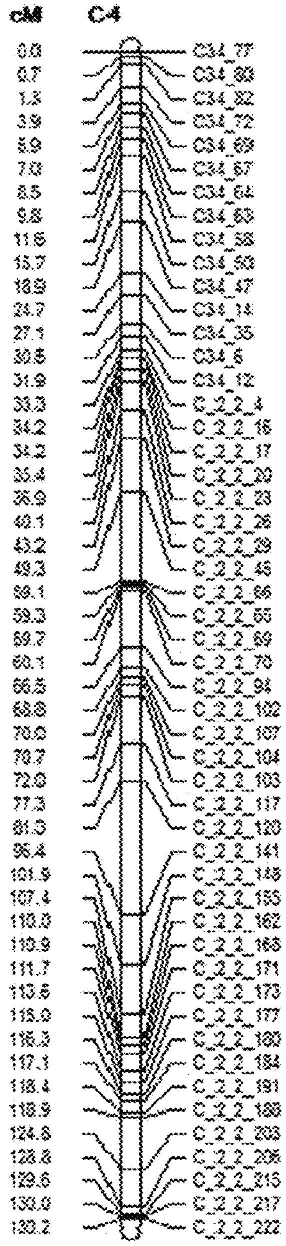
Figure 2E:
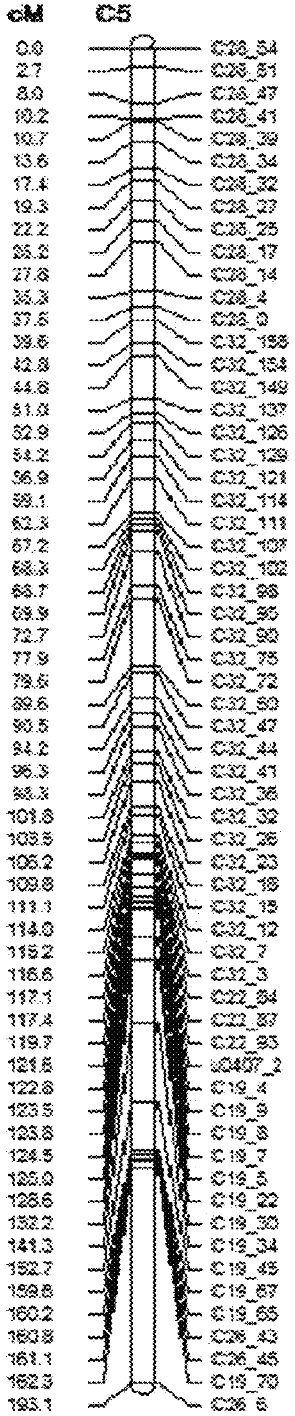
Figure 2F:
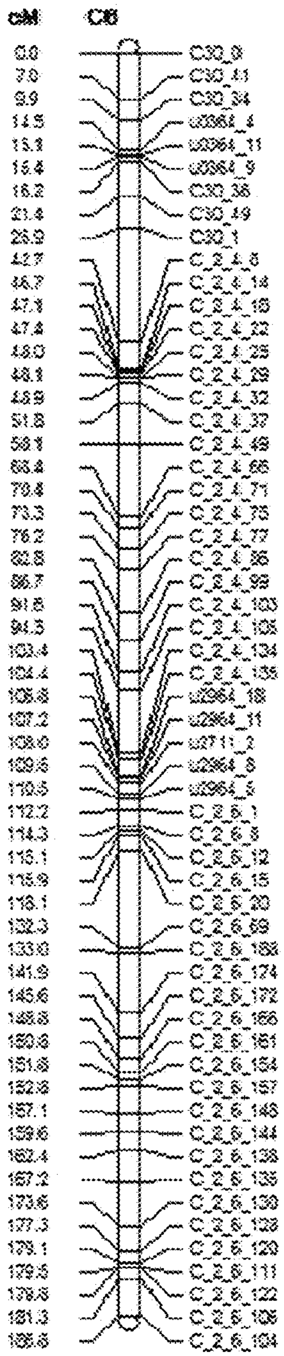
Figure 2G:
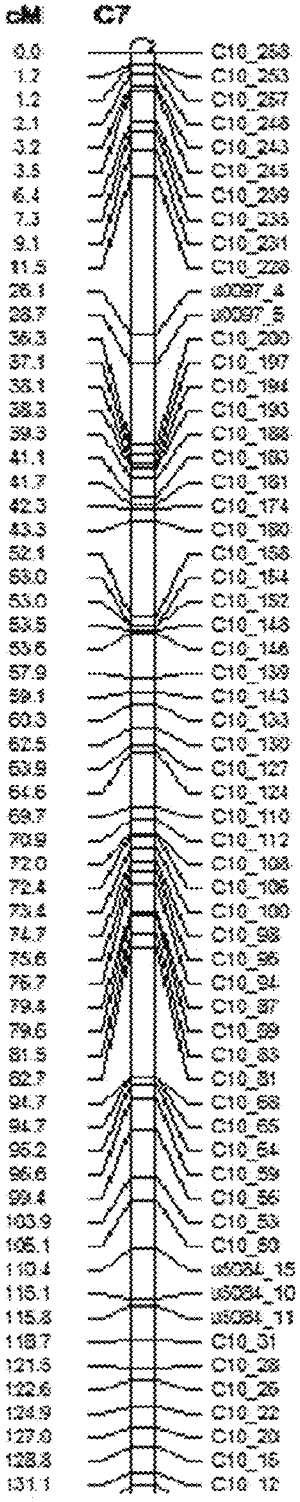
Figure 2H:
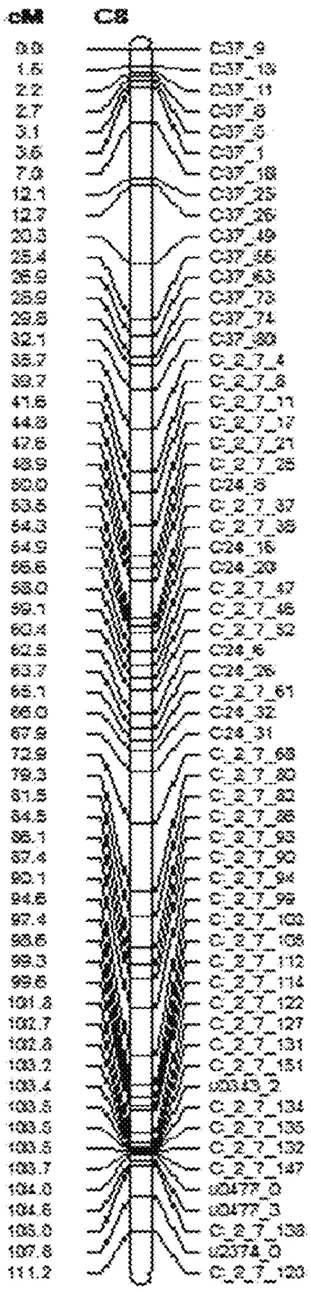
Figure 2I:
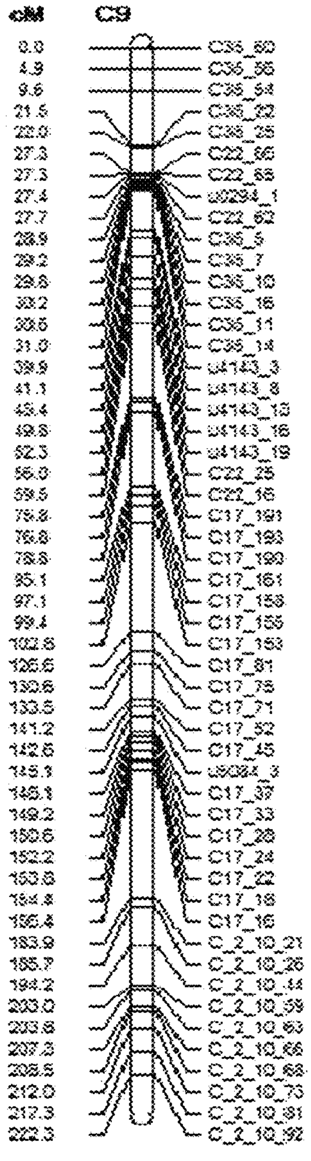
Figure 2J:
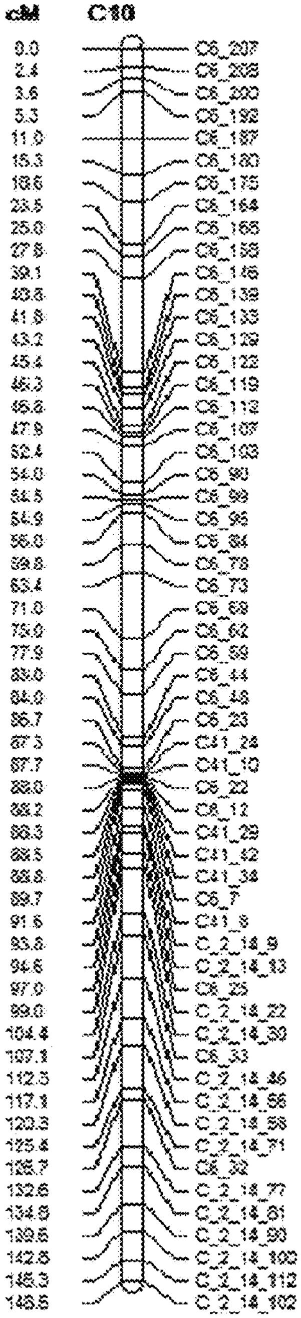
Figure 2K:
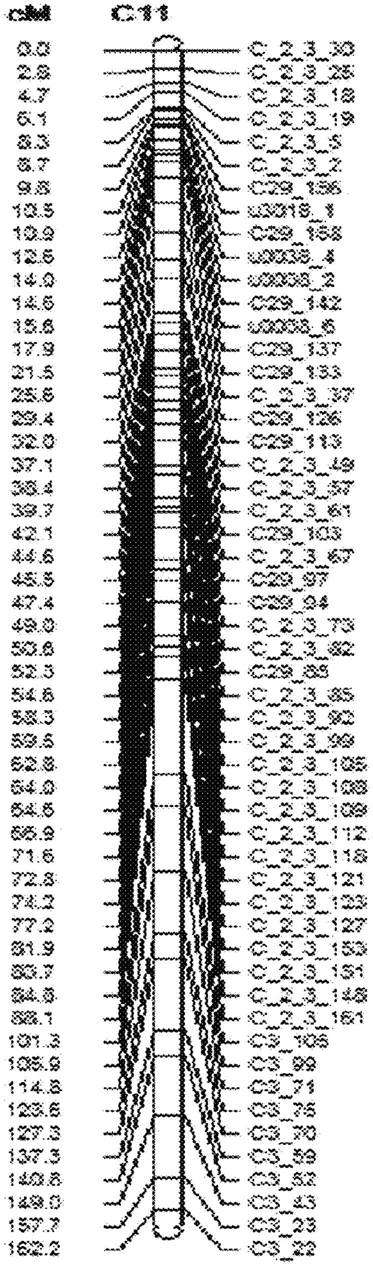
Figure 2L:
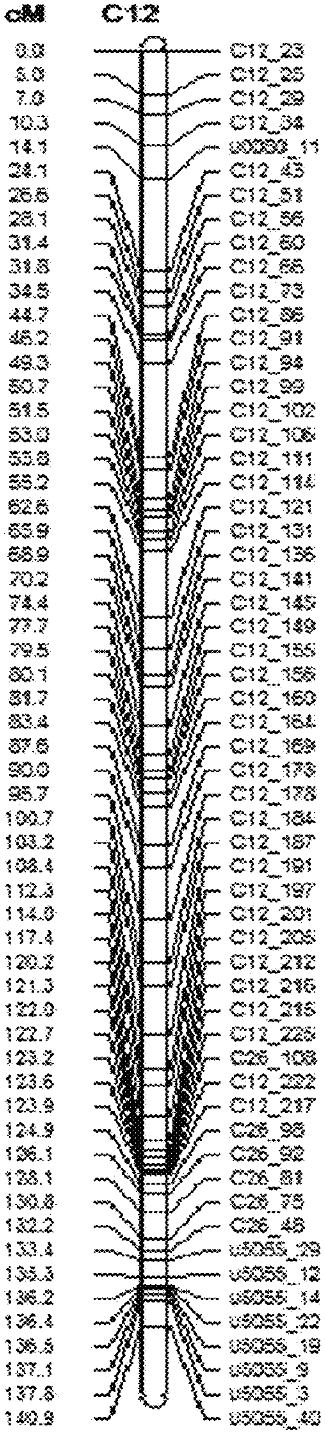
Figure 2M:
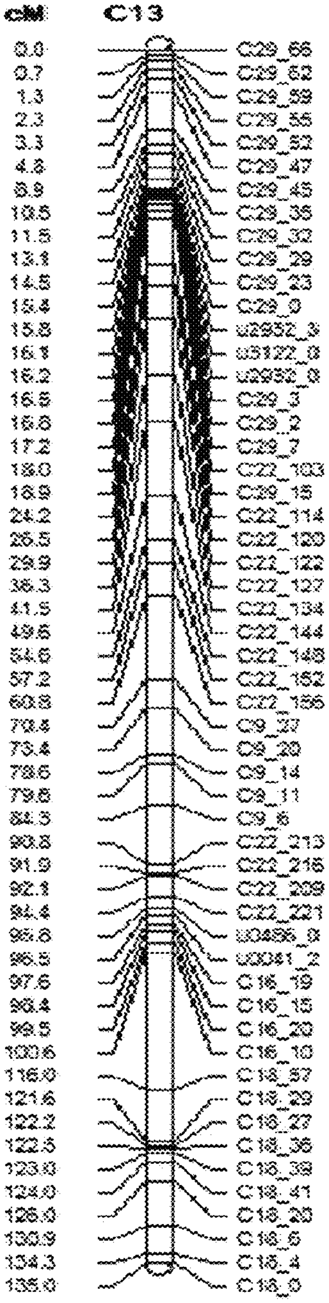

For further illustrating the invention, experiments detailing an Sidt1 gene, a cDNA of the Sidt1 gene, an SNP molecular marker Sidt27-1, and a method for identifying the Sidt1 gene using the SNP molecular marker Sidt27-1 are described below. It should be noted that the following examples are intended to describe and not to limit the invention.

Primary germplasm materials and varieties of sesame used in the invention are briefly introduced hereinbelow:

In the prior art, Yuzhi 11 is an excellent parent material in sesame breeding. New variety Yuzhi DS899 with the determinate growth habit used in the invention was selected from Yuzhi 11 using EMS mutagenesis by Henan Sesame Research Center, Henan Academy of Agricultural Sciences. This new variety has been applied to national new variety protection (application number: 20150395.2) and passed the evaluation of new sesame variety examination in Henan province in 2015. The main traits of Yuzhi DS899 are as follows: determinate growth habit, average capsule nodes of 15-20, three flowers per leaf axil, single stem, four-edge capsule, and white seed coat color.

The sesame resource JS012 is from the germplasm reservoir of Henan Sesame Research Center, Henan Academy of Agricultural Sciences and has the following traits: indeterminate inflorescence, single flower per leaf axil, branched, four-edge capsule, and black seed coat color.

Other sesame materials including 08TP092, Wuninghei, Zhengzhi 98N09, as wild type involved in examples are all from the germplasm reservoir of Henan Sesame Research Center, Henan Academy of Agricultural Sciences. All above germplasm materials are accessible publicly (or from the germplasm reservoir of Henan Sesame Research Center, Henan Academy of Agricultural Sciences) and planted for application.

It should be noted that a thermal cycler PTC-100 (produced by MJ research company) is adopted for performing PCR amplification. Enzymes, buffer and other reagents involved in the PCR amplification were purchased from Shanghai Sangon Biotech Company. Related primers are provided by the GBI China Corporation. PCR reaction of the plant DNA extraction is referred to modified CTAB method (Wei Libin, et. al., Sesame DNA and RNA synchronous extraction method, 2008, Molecular Plant Breeding). Related gene sequencing experiments are accomplished by Tianjin Gene Chip Biology Company.

Example 1 Selection of the Sidt1 Gene and SNP Molecular Marker Sidt27-1

1. Genetic Background of the Determinate Growth Habit Trait

To perform the genetic analysis of the determinate growth habit trait, the direct and the reciprocal crosses were carried out between Yuzhi DS899 and Yuzhi 11, JS012, and Wuninghei having the indeterminate growth habit, respectively (specific combinations of the reciprocal cross were as shown in Table 1), and the inflorescence development type of F1 progeny was investigated. Combinations of the direct and the reciprocal crosses of Yuzhi DS899, Yuzhi 11, JS012, and Wuninghei are shown in Table 1:

TABLE 1

Combinations of the direct and the reciprocal crosses between the determinate and the indeterminate genotypes

| Parental combination | $F_1$ generation | $F_2$ population | BC1 cross |
|---|---|---|---|
| Yuzhi DS899 × Yuzhi 11 | More than 200 plants | Yuzhi DS899 × Yuzhi 11 | Yuzhi DS899 × Yuzhi 11 × Yuzhi DS899 |
| Yuzhi DS899 × JS012 | More than 200 plants | Yuzhi DS899 × JS012 | Yuzhi DS899 × JS012 × Yuzhi DS899 |
| Yuzhi DS899 × Wuninghei | More than 200 plants | Yuzhi DS899 × Wuninghei | Yuzhi DS899 × Wuninghei × Yuzhi DS899 |
| Yuzhi 11 × Yuzhi DS899 | More than 200 plants | | |
| JS012 × Yuzhi DS899 | More than 200 plants | | |
| Wuninghei × Yuzhi DS899 | More than 200 plants | | |

In which, trait comparison of Yuzhi DS899 (the determinate type) and the indeterminate type parent Yuzhi 11 was shown in FIG. 1.

Investigation results of the $F_1$ generation showed that all the $F_1$ population presented normal indeterminate growth habit, which indicated that the mutant trait (determinate inflorescence) is controlled by recessive genes. Thereafter, the $F_2$ progeny of direct crosses of Yuzhi DS899 with Yuzhi 11, JS012, and Wuninghei were cultivated. Each population had exceeding 200 plantlets. Traits were investigated in the filed during the flowering stage, and the results were listed in Table 2.

TABLE 2

Segregation results of the determinate growth habit traits in the $F_2$ generation and its progeny derived from the tested cross

| Hybrid combination | $F_2$ segregation ratio (determinate: indeterminate) | Segregation ratio in test cross population (determinate: indeterminate) |
|---|---|---|
| Yuzhi DS899 × Yuzhi 11 | 64:215 | 94:92 |
| Yuzhi DS899 × JS012 | 78:242 | 108:125 |
| Yuzhi DS899 × Wuninghei | 71:229 | 78:84 |

The above data indicated that the segregation ratios of the determinate phenotype to the wild type were 64:215, 78:242, and 71:229. The fitness test results shown that the segregation results fitted the expected 1:3 segregation ratio, which indicated that the mutant trait is controlled by a recessive gene. Further test was performed using the progeny of top-crosses derived from Yuzhi DS899 and Yuzhi 11, JS012, and Wuninghei, respectively. The progeny segregation ratios of the mutated trait were 94:92, 108:125, and 78:84, respectively. The fitness test results indicated that the determinate growth trait fitted the expected segregation ratio of 1:1, which further demonstrated that the determinate growth trait is controlled by one recessive gene.

2. Construction of $F_2$ Genetic Population Derived from Crossing the Determinate Growth Type Parent and the Indeterminate Growth Type Parent In July, 2013, the new combination between purified Yuzhi DS899 (determinate phenotype) and JS012 (indeterminate phenotype) was performed to acquire an $F_1$ generation.

In November, seeds from the $F_1$ generation of the above combination were dibbled in nutrition pots and planted in Sanya base of Henan Sesame Research Center, Henan Academy of Agricultural Sciences. When two pairs of euphylla came out, the plants were timely transplanted, and the number of plantlets were ensured larger than 200.

3. Construction of the SNP Genetic Map of the $F_2$ Population and the Location of the Sidt1 Gene 1) Resequencing of parent of $F_2$ generation and individual DNAs of 122 $F_2$ plant 120 plants were randomly selected from the $F_2$ population. Young leaves were collected respectively from the 120 $F_2$ plants and 2 parent plants and DNAs were extracted from each plant. Genomes of the 122 materials were re-sequenced using Illumina sequencing method, and the sequencing coverage was ≥30×.

2) The Yuzhi 11 genome was used as the reference genome (Zhang et al., Genome sequencing of the important oilseed crop *Sesamum indicum* L., 2013, Genome Biology; Miao et al., The sesame genome project and genome sequencing. XXII International Plant and Animal Genome Conference (San Diego, USA), 2014 (Conference poster abstract)), and Burrows-Wheeler Aligner (BWA) software was employed to assemble the sequenced data of each plant.

3) The ultra-dense SNP genetic map of the $F_2$ population of sesame was constructed using the Joinmap_linkage map software. As shown in FIGS. 2A-2M, the constructed genetic linkage map comprised 3101 bins and 124 thousand markers in 13 linkage groups. The map had a whole length of 1872.2 cM and an average linkage density of 144.0 cM and an average maker density of 0.014 cM.

Figure 3:
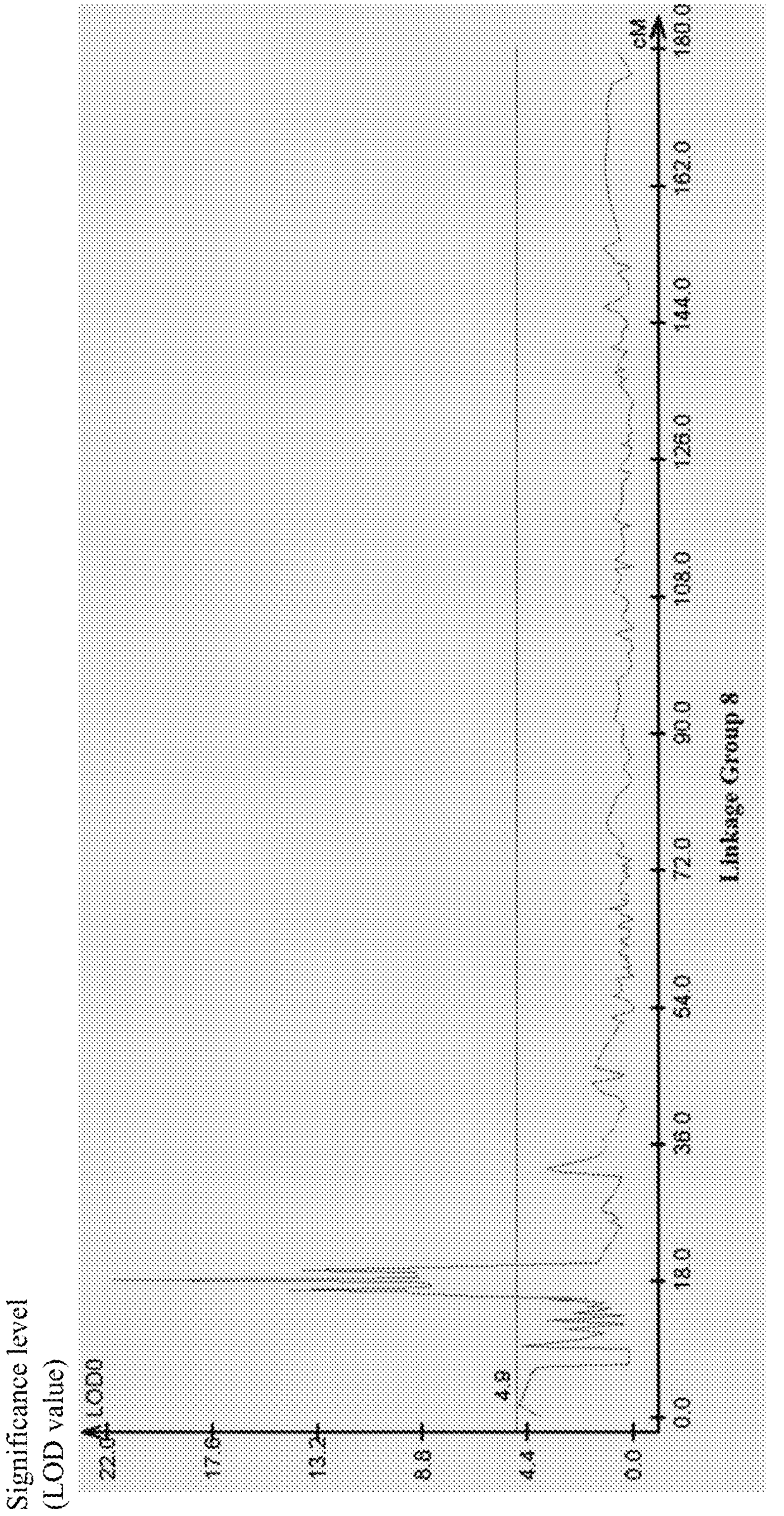
FIG. 3 is a locus result of Sidt1 gene controlling the determinate growth habit of sesame in an SNP genetic map in accordance with one embodiment of the invention.

4) During the early flowering stage—the final flowering stage, the inflorescence type of 120 plants of the $F_2$ population and two parent plants of the $F_2$ generation was investigated. The phenotype investigation was performed for three times. Combined with the above ultra-dense SNP genetic map, the WinQTL cart software was employed to determine one interval coherently linked to the determinate growth habit of sesame, as shown in FIG. 3. It was indicated from the results that the mutant gene was located in the eighth linkage group in the 18.0 cM-19.2 cM inheritance interval, and a physical distance between two markers is approximately 480 kb. It was known from further analysis that the interval contains 15 SNP/InDel polymorphic loci.

Subsequently, the 15 candidate SNP/InDel polymorphic loci were converted into molecular markers (in another word, primers were designed and amplified according to the known sequences in order to acquire the corresponding sequences). The molecular markers of the specific 15 candidate SNP/InDel polymorphic loci were listed as follows in Table 3:

TABLE 3

Molecular markers of the specific 15 candidate SNP/InDel polymorphic loci

| Candidate SNP/InDel | Primer name | Primer DNA sequence (5'-3') | Tm (° C.) | Size of amplified product (bp) |
|---|---|---|---|---|
| Sidt27-1 | HSDt01-1F | CCTGATGTTCCTGGTCCGAA (SEQ ID NO. 4) | 60.4 | 92 |
| | HSDt01-2F | CTATTCCTGATGTTCCTGGTCCGAG (SEQ ID NO. 5) | 61.9 | |
| | HSDt01-R | CTATTCCTGATGTTCCTGGTCCGAG (SEQ ID NO. 6) | 55.5 | |
| Sidt27-2 | HSDt02-F | TTGGGGTTTGGAGTCTTGG (SEQ ID NO. 12) | 57.9 | 77 |
| | HSDt02-1R | AATGATTGATGTCTGTGTGTGTCTA (SEQ ID NO. 13) | 57.3 | |
| | HSDt02-2R | TATTAAATGATTGATGTCTGTGTGTGTCTT (SEQ ID NO. 14) | 58.9 | |

TABLE 3-continued

Molecular markers of the specific 15 candidate SNP/InDel polymorphic loci

| Candidate SNP/InDel | Primer name | Primer DNA sequence (5'-3') | Tm (° C.) | Size of amplified product (bp) |
|---|---|---|---|---|
| Sidt27-3 | HSDt03-F | ATTACTCCATAGTCGAGGAAGAAAC (SEQ ID NO. 15) | 57.8 | 96 |
| | HSDt03-1R | ACACCTTAATAGAAAAACAAAATCA (SEQ ID NO. 16) | 57.5 | |
| | HSDt03-2R | TATATACACCTTAATAGAAAAACAAAATCG (SEQ ID NO. 17) | 58.9 | |
| Sidt27-4 | HSDt04-1F | ACAATTAATACATGTATATGTGCCC (SEQ ID NO. 18) | 55.7 | 112 |
| | HSDt04-2F | TATATACAATTAATACATGTATATGTGGCG (SEQ ID NO. 19) | 59.1 | |
| | HSDt04-R | CTCTCTCCCTCTCTCATACACAAAT (SEQ ID NO. 20) | 58.2 | |
| Sidt27-5 | HSDt05-F | AAGTTTTGAACCAACGTAAACA (SEQ ID NO. 21) | 56.8 | 74 |
| | HSDt05-1R | ATTGATCAGTAAAGATTATCATGGT (SEQ ID NO. 22) | 52.4 | |
| | HSDt05-2R | ATATAATTGATCAGTAAAGATTATCATGGC (SEQ ID NO. 23) | 53.8 | |
| Sidt27-6 | HSDt06-1F | TGCTCAACCTCCATTTGGCG (SEQ ID NO. 24) | 59.2 | 103 |
| | HSDt06-2F | TATATTGCTCAACCTCCATTTGGCA (SEQ ID NO. 25) | 62 | |
| | HSDt06-R | CAACACGTGCTATCATCTGAATC (SEQ ID NO. 26) | 57.6 | |
| Sidt27-7 | HSDt07-1F | CGCAGGTTTTATTCTGATATACTG (SEQ ID NO. 27) | 59.9 | 103 |
| | HSDt07-2F | ATATACGCAGGTTTTATTCTGATATACTA (SEQ ID NO. 28) | 61.5 | |
| | HSDt07-R | ACTCTCGTACTTCTCTCTTGAACCC (SEQ ID NO. 29) | 59.7 | |
| Sidt27-8 | HSDt08-1F | AAATAACAAAGGTGTAAATCATTCC (SEQ ID NO. 30) | 59.3 | 114 |
| | HSDt08-2F | AATATAAATAACAAAGGTGTAAATCATTCT (SEQ ID NO. 31) | 60.8 | |
| | HSDt08-R | AGTAGTCGCCATAAACTATAACTCA (SEQ ID NO. 32) | 55.3 | |
| Sidt27-9 | HSDt09-F | CACAATTTTCTCATTTCACTCGGAA (SEQ ID NO. 33) | 62.7 | 87 |
| | HSDt09-1R | TAGGATGTGGGTTTGTTCTATACAT (SEQ ID NO. 34) | 55 | |
| | HSDt09-2R | TATATTAGGATGTGGGTTTGTTCTATACAG (SEQ ID NO. 35) | 56.4 | |
| Sidt27-10 | HSDt10-F | AATCAATTGGTAAGGATGGTATCA (SEQ ID NO. 36) | 57.7 | 193 |
| | HSDt10-R | TTATTCGTCACTTACAGATTATCCA (SEQ ID NO. 37) | 56.2 | |
| Sidt27-11 | HSDt11-F | GCATTTAGAATTACGTTTTAATCTCC (SEQ ID NO. 38) | 58.3 | 130 |
| | HSDt11-R | AACCGTTATTGAAATAGTCTATTGG (SEQ ID NO. 39) | 56.9 | |
| Sidt27-12 | HSDt12-F | TATTATTGCCGTTCTTATTGTTTTT (SEQ ID NO. 40) | 57.7 | 99 |
| | HSDt12-R | CGTCATTTTTTTGGTTATATTTCTA (SEQ ID NO. 41) | 56 | |
| Sidt27-13 | HSDt13-F | TGGATAAGCATACACACACCAACAT (SEQ ID NO. 42) | 61.3 | 129 |
| | HSDt13-R | AACTTGCTGCAGAGGGACTCG (SEQ ID NO. 43) | 60.4 | |
| Sidt27-14 | HSDt14-F | GCCGCAATTTAATTTCTTTCA (SEQ ID NO. 44) | 57.9 | 166 |
| | HSDt14-R | GACTAGAGACTCCCCACACTTAGAT (SEQ ID NO. 45) | 57.4 | |

TABLE 3-continued

Molecular markers of the specific 15 candidate SNP/InDel polymorphic loci

| Candidate SNP/InDel | Primer name | Primer DNA sequence (5'-3') | Tm (° C.) | Size of amplified product (bp) |
|---|---|---|---|---|
| Sidt27-15 | HSDt15-F | TTTTTAGCCGTATTCCGAGACTAT (SEQ ID NO. 46) | 59.3 | 187 |
| | HSDt15-R | ATGGCTCTATCTACCAAAATCTAAT (SEQ ID NO. 47) | 55.8 | |

Figure 4:
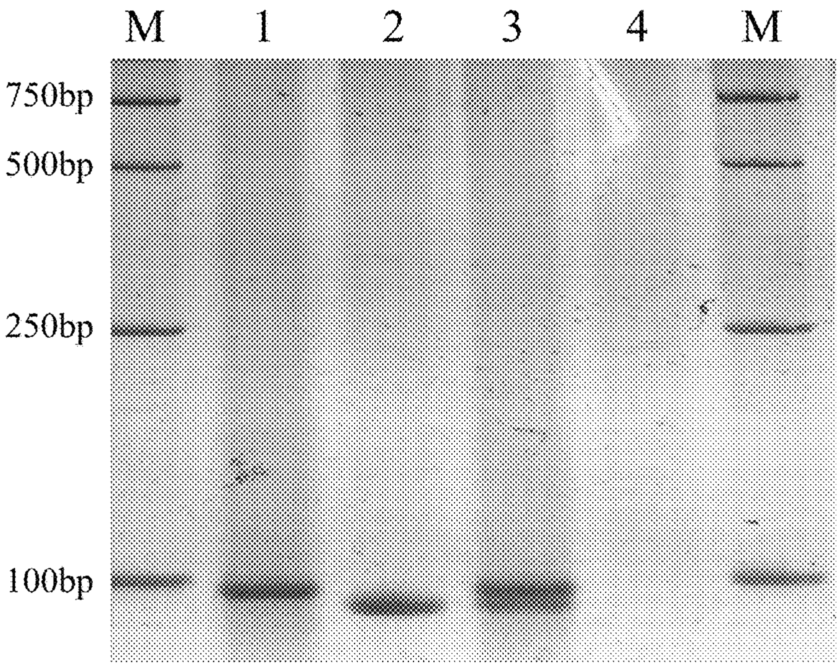
FIG. 4 shows PCR amplification results of some germplasm materials of sesame using primer pairs of HSDt01-1F, HSDt01-2F, and HSDt01-R of an SNP marker Sidt27-1, in which lane M: DL 2000 marker indicating partial DNA bands of 750 bp, 500 bp, 250 bp, and 100 bp from top down; lane 1 indicates Yuzhi 11 (indeterminate inflorescence type) containing allele 2 (dt0 type) of Sidt1; lane 2 indicates a determinate inflorescence type containing allele 1 (dt1 type) of Sidt1; lane 3 is a hybrid material of $F_1$ generation derived from cross combination of Yuzhi 11×Yuzhi DS899; and lane 4 is PCR amplification control result using water as a template.

50 plants were randomly selected from the parent plants and the $F_2$ population to extract DNAs therefrom, and the 15 primer pairs of molecular markers were utilized to evaluate the association relationship. The results demonstrated that only Sidt27-1 locus was tightly associated with the determinate growth habit trait (as shown in FIG. 4).

Example 2 Gene Cloning and Gene Sequence Analysis of the Sidt1 Gene

On the basis of Example 1, PCR amplification was applied to obtain the related sequences, and the amplification product was sequenced to obtain the specific sequence of the Sidt1 gene. The processes were introduced as follows:

1) According to the SNP locus acquired in Example 1 and the genome data of Yuzhi 11, the gene sequence containing the Sidt27-1 locus was determined. The gene sequence was denominated as Sidt1. The sequence analysis of Sidt1 showed that the gene was annotated as TEL gene (SiDt) in the genome of sesame (Yuzhi 11).

Thereafter, software Primer premier 5.0 was utilized to design the primer pair for amplifying the Sidt1 gene according to the genome data, which were specifically as follows:

```
Sequence of forward primer Dt1 Primer F (SEQ ID
NO. 7):
5'-ATGGCAAAAATGTCATCGGACC-3';
and

Sequence of reverse primer Dt1 Primer R (SEQ ID
NO. 8):
5'-CTAGCGCCTTCTAGCAGCAGTC-3'.
```

PCR amplification was then performed using DNA of Yuzhi DS899 as a template.

PCR procedure was as follows: 94° C. for 3 min, 30 cycles of 30 s at 94° C., 30 s at 55° C., 1 min at 72° C., and a final 5 min extension at 72° C. PCR amplification products were preserved at 4° C., or the amplification bands were directly recovered and sequenced.

Figure 5:
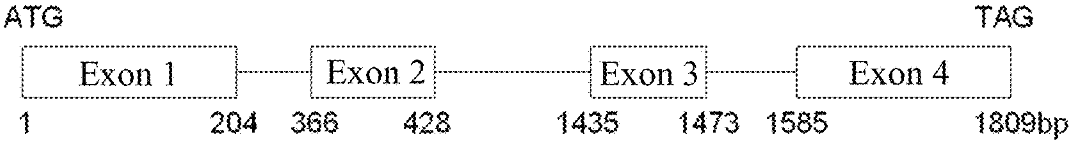
FIG. 5 is a gene structure of Sidt1 for controlling the determinate growth habit of sesame.

The results indicated that the DNA sequence of the gene had a length of 1809 bp, including 4 exons and 3 introns (as shown in FIG. 5), the sequence of which was listed as SEQ ID NO. 1.

In the meanwhile, the above primer pair was adopted to amplify the DNA of Yuzhi 11 and the amplified products were sequenced.

Figure 6:
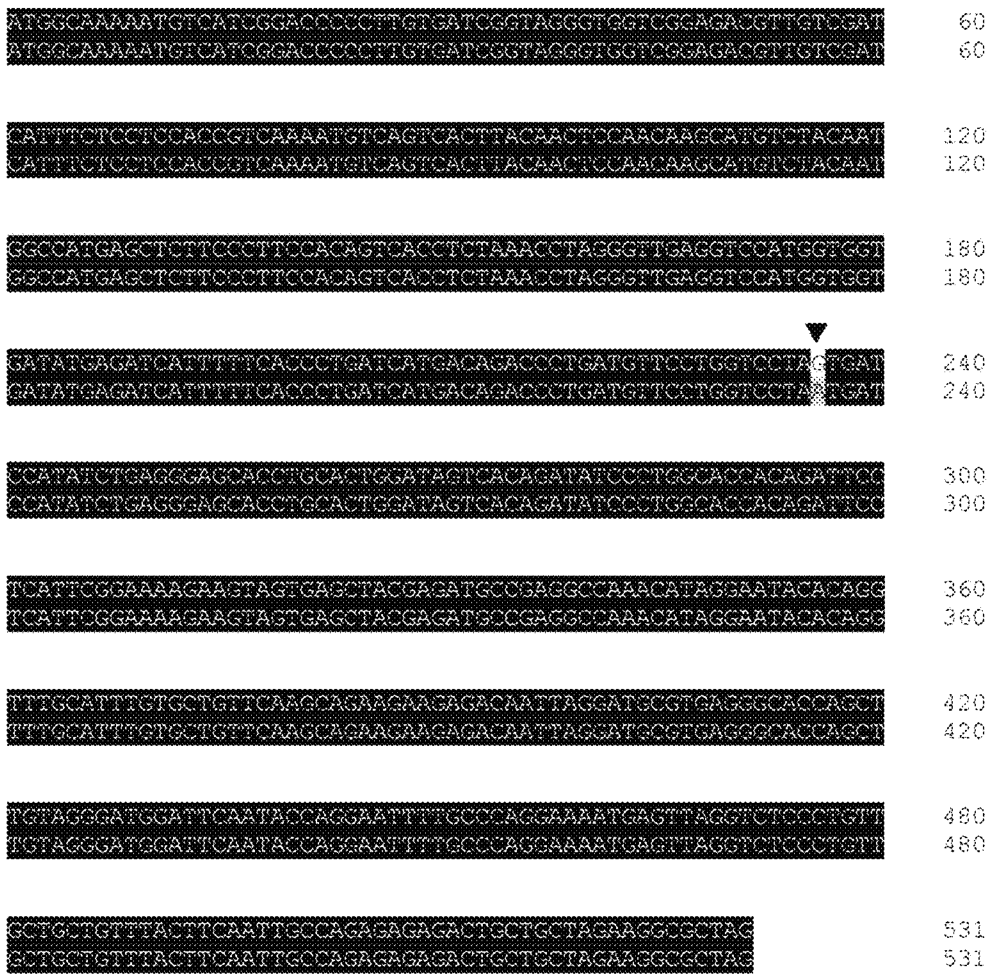
FIG. 6 is sequence alignment result of a Sidt1 gene for controlling the determinate growth habit and a SiDt allele of normal germplasm with indeterminate growth habit (which is annotated as Sitfl in sesame reference genome), in which: an arrow indicates differentiated locus between the nucleotide sequences of Sidt1 gene and SiDt allele, an upper row is a cDNA sequence (SEQ ID NO. 9) of the SiDt allele of the normal variety with indeterminate growth habit, and a lower row is a cDNA sequence (SEQ ID NO. 2) of the Sidt1 gene.
Figure 7:
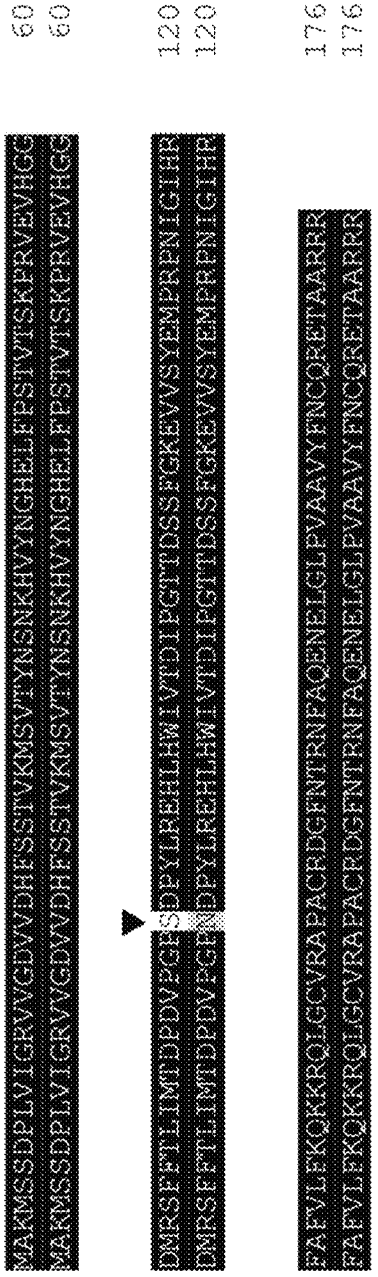
FIG. 7 is amino acid sequence alignment results encoded by Sidt1 gene for controlling the determinate growth habit and SiDt allele of normal varieties with indeterminate growth habit, in which, an arrow indicates differentiated locus in amino acid sequences of Sidt1 protein and SiDt protein, an upper row is an amino acid sequence (SEQ ID NO. 10) encoded by the SiDt allele of normal varieties with indeterminate growth habit, and a lower row is an amino acid sequence (SEQ ID NO. 11) encoded by the Sidt1 gene.

The Sidt1 gene was aligned with SiDt allele of wild type (Yuzhi), results of which were shown in FIG. 6. It was known from FIG. 6 that the difference of the Sidt1 between the genomes of the determinate and the indeterminate growth germplasm materials is whether G/A mutation occurred at the 236th base in the coding region. When the inflorescence type was mutated from the indeterminate type into the dt1 determinate type, the 236th base of the coding region was mutated from the "G" base into the "A" base, resulting in the mutation from serine (S) into asparagine (N) at the 79th amino acid in the encoded protein sequence (as shown in FIG. 7).

2) According to the DNA extraction method as described in the above, RNA was extracted from young plants of Yuzhi DS899 and TaKaRa RNA reverse transcription kit (purchased from TaKaRa company) was utilized to perform the reverse transcription to acquire total cDNA. PCR amplification was performed according to the instruction for use of the reverse transcription kit.

It should be noted that during the reverse transcription process, the primer pairs utilized in the PCR reactions were designed as follows:

```
TFL1 CDs-F (SEQ ID NO. 7):
5'-ATGGCAAAAATGTCATCGGACC-3;

TFL1 CDs-R (SEQ ID NO. 8):
5'-CTAGCGCCTTCTAGCAGCAGTC-3'.
```

The PCR reaction was performed to amplify a sequence of the coding region of the cDNA of Sidt. PCR products were then sequenced to yield the cDNA sequence of the Sidt1 gene, which had a length of 531 bp, encoding 176 amino acids, and having a sequence presented by SEQ ID NO. 2.

3) For demonstrating the SNP locus of the Sidt1 gene, the SNP primer pairs of the Sidt1 gene were designed according to Wei et. al., (Development of SNP and InDel markers via de novo transcriptome assembly in *Sesamum indicum* L., 2014, Molecular Breeding). It should be explained that in order to distinguish different SNP alleles in the genome, two aspects must be noted as follows:

First, the SNP primer pair was designed to be three primers, and mismatching was required to be introduced into a third base at a 3' end of the specific primer to enhance the specificity of the amplicons. The principle for introducing the mismatching was as follows: the third mismatching base at the 3' end of the primer was able to form stable complementary mismatch structure with the SNP mismatching base at the 3' end, that was, strong dismatching type (C/T or G/A) and weak dismatching type (C/A or G/T) were coordinated, and medium dismatching type (A/A, C/C, G/G, or T/T) and medium dismatching type were coordinated.

Second, to one of two forward or reverse primers containing the SNP locus, five bases were randomly added to the 5' end of the primer sequence, primarily for the purpose of distinguishing the PCR products of different loci much easier in subsequent gel electrophorogram.

Primer pairs of SNP loci designed by software Primer premier 5.0 were as follows:

a forward primer HSDt01-1F represented by SEQ ID NO. 4:
5' CCTGATGTTCCTGGTCCGAA 3';

a forward primer HSDt01-2F represented by SEQ ID NO. 5:
5' CTATTCCTGATGTTCCTGGTCCGAG 3';

a reverse primer HSDt01-R represented by SEQ ID NO. 6:
5' TAAATCAATCAGGTCTTAAGCAGT 3';

It should be noted that when the forward primer HSDt01-1F matched with the reverse primer HSDt01-R, the amplified product had a band size of 92 bp (dt1 type); when the forward primer HSDt01-2F matched with the reverse primer HSDt01-R, the amplified product had a band size of 96 bp (dt2 type).

To identify the Sidt1 gene to be the gene controlling the inflorescence development type in sesame, $F_2$ populations of three combinations were constructed for validation. These $F_2$ populations were specifically as follows: $F_2$ progeny derived from three combinations of Yuzhi DS899×Yuzhi 11, Yuzhi DS899×JS012, and Yuzhi DS899×Wuninghei, respectively were constructed, and 50 lines were randomly selected from the $F_2$ progeny, and in the meanwhile, the inflorescence phenotype of each line were investigated in the field.

50 plantlets were randomly selected from the 50 lines, and young leaves were collected from the 50 plantlets and 4 parent plantlets. DNAs were extracted from each plant and used as templates for performing PCR amplification, respectively.

PCR reaction adopted a 10 μL reaction system, which was as follows:

Template DNA (50 ng/μL), 1.0 μL;
10×PCR Buffer ($Mg^{2+}$), 1.0 μL;
Taqase (5 U/μL), 0.2 μL;
dNTP (10 mmol/L), 0.2 μL;
Forward Primer 1 (10 μM), 0.5 μL;
Forward specific Primer 2 (10 μM), 0.5 μL;
Reverse Primer (10 μM), 1.0 μL; and
Added with ultrapure water 5.6 μL.

The PCR procedure was as follows: 94° C. for 3 min, 30 cycles of 30 s at 94° C., 30 s at 55° C., 30 s at 72° C., and a final 5 min extension at 72° C. PCR products were preserved at 4° C.

PCR products were conducted with non-denaturing polyacrylamide gel electrophoresis analysis, in which, a gel concentration was between 8 and 10 wt. %, a gel size was 180 mm×120 mm×2 mm, an electrophoresis buffer was 0.5×TBE, and the electrophoresis was performed at 150V AC voltage for 1.5 to 2 hours. After the electrophoresis, 0.1% silver nitrate solution was added to the gel and a resulting mixture was placed on a horizontal shaker for 10 minutes. Then 2% sodium hydroxide and 0.4% formaldehyde mixed solution were added for appropriateness color developing in horizontal shaker. Finally, the gel was rinsed with water and data was read and recorded.

Figure 8:
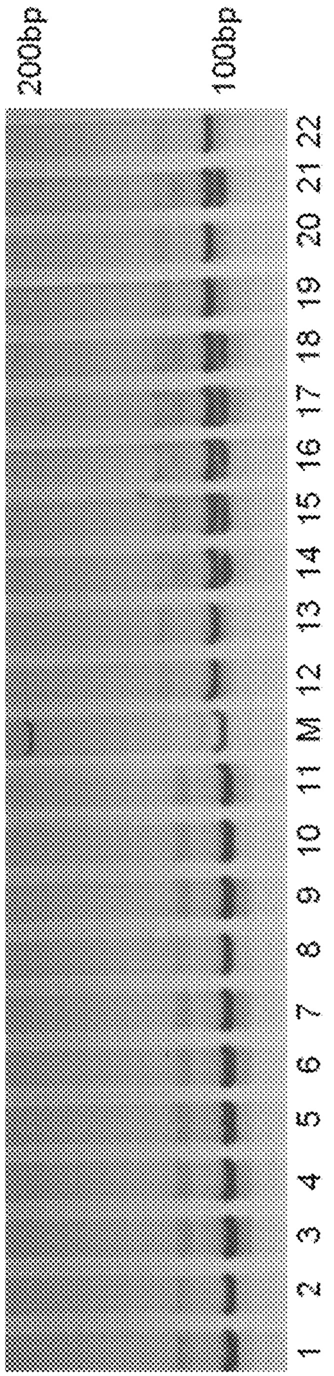
FIG. 8 is PCR identification results of primer pairs of SNP marker Sidt27-1, i. e., HSDt01-1F, HSDt01-2F, and HSDt01-R in $F_2$ population, in which, lane M is a DL 2000 marker, indicating bands having sizes of 200 bp and 100 bp from top down; lanes 1-11 indicate $F_2$ plants with homozygous Sidt1 locus (determinate inflorescence type); lanes 12, 13, 19, 20, and 22 indicate $F_2$ plants with homozygous SiDt allele (indeterminate inflorescence type); and lanes 14-18 and 21 indicate $F_2$ plants with heterozygous Sidt1/SiDt (indeterminate inflorescence type)

A part of an electrophoresis photograph was shown in FIG. 8.

The results indicated that plants with determinate phenotype had the amplicon with a band size of 92 bp, parent plants with indeterminate phenotype had the amplicon with a band size of 97 bp, and hybrid plants had amplicons with band sizes of 92 bp and 97 bp and the phenotype was indeterminate.

Thus, Sidt1 was considered as the gene causing the mutation of the determinate growth habit in sesame and was adaptable to the study of the inflorescence development in crops.

Example 3 Sequence Analysis of Sidt1 Gene

To further identify the characteristics of the Sidt1 gene and in the meanwhile identify the copy number thereof in the genome of sesame, Southern hybrid blotting was performed.

1) Design and preparation of Southern hybridization probe of the Sidt1 gene

Software Primer Premier 5.0 was utilized to design the primer pair according to genome DNA and SiDt sequence of Yuzhi 11, and the primer pair was specially as follows:

Forward primer of Dt-Gs (SEQ ID NO. 48):
5'-GAGCCCTCTTTCAAAAACACC-3';
and

Reverse primer of Dt-Gs (SEQ ID NO. 49):
5'-AGCAGCAACAGGGAGACCTA-3'.

Genome DNA of Yuzhi 11 as the template and the primer pairs Dt-Gs was adopted for PCR amplification, and PCR products had a band size of 459 bp.

Ingredients and volumes for the PCR reaction were as follows:

Template DNA (50 ng/μL), 2.0 μL;
10×PCR Buffer ($Mg^{2+}$), 5.0 μL;
Taqase (5 U/μL), 0.5 μL;
dNTP (10 mmol/L), 1.0 μL;
Forward primer Dt-Gs (10 μM), 1.0 μL;
Reverse primer (10 μL), 1.0 μL;
Added with ultrapure water to a total volume of 50 μL;

The PCR reactions were carried out under the following conditions: 94° C. for 3 min, 30 cycles of 30 s at 94° C., 30 s at 55° C., 30 s at 72° C., and a final 5 min extension at 72° C. PCR amplified products were preserved at 4° C.

The PCR products were detected by 1% agarose gel electrophoresis and sequenced for identification.

The PCR products were used as the Southern hybridization probes, and DIG-High Prime DNA Labeling & Detection Starter Kit I (Roche company) was utilized for performing probes labeling and detection. Specific processes were performed following the instruction of DIG-High Prime DNA Labeling & Detection Starter Kit I.

2) Construction of recombinant standard plasmid

The probe fragments obtained in the above step 1) were inserted into a vector pGEM-T Easy to construct a pGEM-T Easy plasmid carried with the probe fragments, which was used as a positive control of the Southern hybridization.

Processes including ligation, recovery, and purification of the plasmid were accomplished using ligation and recovery kits (related regents and kits were all purchased from Promega corporation), and the quality of the plasmid was detected by 0.8% agarose gel electrophoresis.

The pGEM-T Easy plasmids carried with the probe sequence was extracted using DNA extraction kit (TaKaRa company), and diluted to a concentration of between 1 and 5 μg/L for subsequent Southern blotting. Specific processes were performed according to the instructions of DNA extraction kit.

3) Southern blotting of the Sidt1 gene 200 g of young leaves of three sesame varieties of Yuzhi 11, Yuzhi Ds899, and *S. raditum* (wild species) were respectively collected and DNAs of each plant were extracted.

10 μg of the genome DNAs of the three varieties were respectively collected and digested by two restriction endonuclease enzymes of HindIII and EcoRI for 16 h, and the digested products were recovered and purified using the recovery kit (related enzyme reagents and recovery kits were all purchased from TaKaRa company, and specific processes thereof were carried out according to the instructions of the kits).

Figure 9:
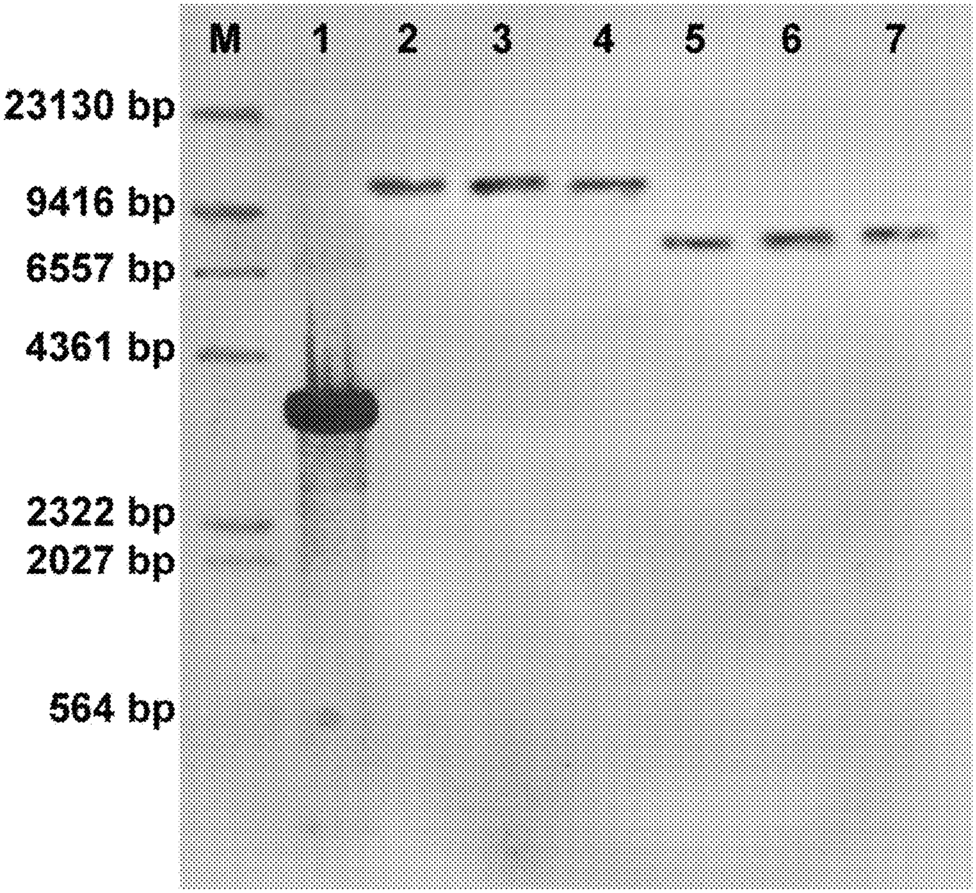
FIG. 9 is a southern blot hybridization result of a Sidt1 gene and SiDt allele of normal varieties, in which, lane 1 indicates the hybridization blots of positive plasmid comprising probe sequence of the SiDt gene of the normal variety; lane 2-4 indicate hybridization results of genome DNAs of Yuzhi 11 (wild type, indeterminate, dt0) restricted by Hind III, Yuzhi DS899 (determinate, dt1), and wild type *S. raditum* (dt0, indeterminate), respectively from left to right; and lane 5-7 indicate hybridization results of genome DNAs of Yuzhi 11 (wild type, indeterminate, dt0) restricted by Hind III and EcoR I, Yuzhi DS899 (determinate, dt1), and wild type *S. raditum* (dt0, indeterminate), respectively from left to right.

The digested products were properly concentrated, labeled by digoxin, and applied for Southern hybridization. Specific hybridization process was as follows:

The electrophoresis of the digested DNA products was performed with 0.7% gel at a constant voltage of 25 V, 4° C. for overnight. Then the DNA products were transferred to hybridization membrane, and hybridized with probes, and the membrane was then washed. Southern hybridization results were recorded, as shown in FIG. 9.

Specific processes and operations of Southern hybridization were carried out according to the instructions of digoxin labeled Southern blotting kit (Roche company).

It was known from the results of Southern hybridization that in the determinate (dt1 type) and the indeterminate (dt0 type) sesame germplasm, the Sidt1 and the SiDt allele were all hybridized. The hybridized band was sole and the size thereof was approximately the same. This result indicated that the Sidt1 and the allele all existed with single copy in the genomes of the cultivated or the wild type germplasm with the two inflorescence growth phenotypes. The difference existed in the gene sequences of the Sidt1 and the allele thereof is very slight.

Example 4 Development of SNP Molecular Marker Sidt27-1 of Sidt1 Gene

As exhibiting the selection process of breeding materials with high yield, high quality, and the determinate growth habit, the example introduced the specific application of the SNP molecular marker Sidt27-1 of the Sidt1 gene.

1) In order to breed materials with high yield, high quality, and the determinate growth habit, Zhengzhi 98N09 was selected from the sesame germplasm reservoir as a female parent, and Yuzhi DS899 was selected as a male parent and the two parents were planted in Yuanyang experimental base of Henan Sesame Research Center, Henan Academy of Agricultural Sciences in June 2014. Cross combination was performed to get $F_1$ population in July, 2014. Seeds of the $F_1$ population were sowed in Sanya base in November, 2014, and plants were self-pollinated in inbred net, then seeds of the $F_2$ generation were obtained, and the $F_2$ population has larger than 200 plantlets. In February, 2015, healthy seeds were randomly selected from 50 plantlets of $F_2$ generation and planed in Sanya base of Hainan. The inflorescence development type of the $F_2$ progeny was investigated. Each line was planted with three repeats, and 10 plantlets per each repeat were investigated.

2) Reliability of SNP markers was evaluated using the three primers (forward primer HSDt01-1F, forward primer HSDt01-2F, reverse primer HSDt01-R) of Example 2.

50 plantlets were randomly selected from the $F_2$ population and two parent plantlets were selected. DNAs were extracted from each plant and used as templates for PCR amplification.

PCR reaction adopted a 10 μL reaction system, which was as follows:

Template DNA (50 ng/μL), 1.0 μL;

10×PCR Buffer ($Mg^{2+}$), 1.0 μL;

Taqase (5 U/μL), 0.2 μL;

dNTP (10 mmol/L), 0.2 μL;

Forward Primer 1 (10 μM), 0.5 μL;

Forward specific Primer 2 (10 μM), 0.5 μL;

Reverse Primer (10 μM), 1.0 μL;

Added with ultrapure water 5.6 μL.

The PCR procedure was as follows: 94° C. for 3 min, 30 cycles of 30 s at 94° C., 30 s at 55° C., 30 s at 72° C., and a final 5 min extension at 72° C. PCR amplified products were preserved at 4° C.

3) Non-denaturing polyacrylamide gel electrophoresis analysis for separating amplified products PCR products yielded from 2) were analyzed with non-denaturing polyacrylamide gel electrophoresis, in which, the gel concentration was between 8 and 10 wt. %, the gel size was 180 mm×120 mm×2 mm, the electrophoresis buffer was 0.5×TBE, and treatment was electrophoresis at 150V AC voltage for 1.5 to 2 h. After the electrophoresis, 0.1% silver nitrate solution was added to the gel and a resulting mixture was silver-dyed on a horizontal shaker for 10 min. Then 2% sodium hydroxide and 0.4% formaldehyde mixed solution were added for appropriate color developing on horizontal shaker. Finally, the gel was rinsed with water and the band data was read and recorded.

A part of an electrophoresis photograph was shown in FIG. 8.

4) Consistence of the detection results of the SNP molecular marker with the phenotypes of the test samples It was known from the screening process of the Sidt27-1 that theoretically, plants containing the allele 1 of Sidt27-1 (a band size of 92 bp, i. e., Sidt27-1 locus) present determinate; plants containing the allele 2 of Sidt27-1 (a band size of 97 bp, i. e., when a "G" base in the Sidt27-1 locus is mutated into an "A" base) present indeterminate; and plants containing the allele 1 and allele 2 of Sidt27-1 (band sizes of 92 bp and 97 bp) are hybrid plants and present the indeterminate inflorescence.

The phenotype investigation results indicated that all the 20 plants containing the allele 1 of Sidt27-1 (the band size of 92 bp) presented determinate, and the reliability was 100%. All the 15 plants containing the allele 2 of Sidt27-1 (the band size of 97 bp) presented indeterminate, and the reliability was 100%. All the 15 plants containing the allele 1 and allele 2 of Sidt27-1 (band sizes of 92 bp and 97 bp) were hybrid plants and presented indeterminate inflorescence, and the reliability was 100%.

Figure 10:
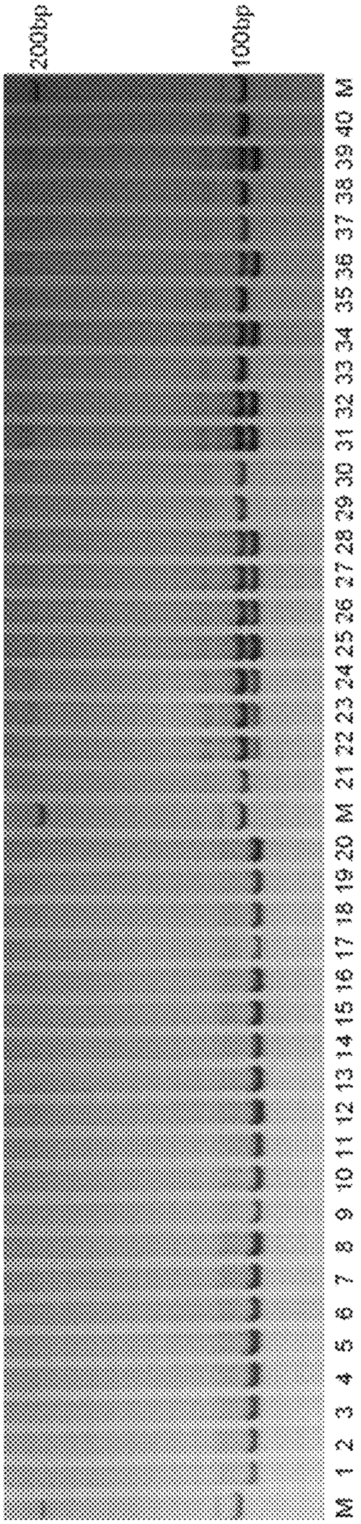
FIG. 10 is application of an SNP molecular marker Sidt27-1 in selection of breeding material, in which, lane M indicates DL 2000 marker; lanes 1-20 indicate $F_2$ plants of homozygous Sidt1 (determinate inflorescence type); lanes 21, 29, 30, 33, 35, 37, 38, and 40 indicate $F_2$ plants carrying homozygous SiDt (indeterminate inflorescence type); and lanes 22-28, 31, 32, 34, 36, and 39 indicate $F_2$ plants carrying heterozygous Sidt1/SiDt (indeterminate inflorescence type).

PCR amplification results of a part of the plants were shown in FIG. 10.

In summary, the SNP marker was demonstrated to be the SNP molecular marker for the Sidt1 gene, which was adapted to predicting the inflorescent development type of the sesame varieties, to molecular marker-assisted breeding and the breeding of the new sesame varieties having the determinate growth habit.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An Sidt1 gene for controlling a determinate growth habit of sesame, the Sidt1 gene consisting of four exons and three introns, wherein a DNA sequence of the Sidt1 gene consists of SEQ ID NO. 1.

2. A cDNA sequence of an Sidt1 gene consisting of a DNA sequence of SEQ ID NO. 1, wherein the cDNA sequence consists of SEQ ID NO. 2.

3. An SNP molecular marker Sidt27-1 being located at a base sequence from 378 to 469 of SEQ ID NO. 1, wherein a DNA sequence of the SNP molecular marker Sidt27-1 consists of

```
SEQ ID NO. 3:
CCTGATGTTCCTGGTCCTAATGATCCATATCTGAGGGAGCACCTGCACTG
GTATGCTTTCATTTTTAACTGCTTAAGACCTGATTGATTTAA.
```

4. A method for identifying the Sidt1 gene using the SNP molecular marker Sidt27-1 of claim 3, the method comprising:

1) extracting a genome DNA of a germplasm material of sesame to be identified;

2) using an extracted DNA of 1) as a template for PCR amplification by using the following primers:

```
a forward primer HSDt01-1F represented by SEQ ID
NO. 4:
5' CCTGATGTTCCTGGTCCGAA 3';

a forward primer HSDt01-2F represented by SEQ ID
NO. 5:
5' CTATTCCTGATGTTCCTGGTCCGAG 3';
and

a reverse primer HSDt01-R represented by SEQ ID
NO. 6:
5' TAAATCAATCAGGTCTTAAGCAGT 3';
```

performing gel electrophoresis on PCR amplified products, and determining whether the genome DNA of the germplasm material of sesame to be identified comprises the SNP molecular marker Sidt27-1 according to the following rules:

if the genome DNA only comprises the SNP molecular marker Sidt27-1, when the primer pair HSDt0I-1F and HSDt01-R are adopted for PCR amplification and a product having a band size of 92 bp is amplified, the germplasm material of sesame is determined to belong to a dt1 type having a determinate growth habit and is adapted to cultivate sesame varieties with the determinate growth habit;

if the genome DNA is in the absence of the SNP molecular marker Sidt27-1, when the primer pair HSDt01-2F and HSDt01-R are adopted for PCR amplification and a product having a band size of 97 bp is amplified, the germplasm material of the sesame is determined to belong to a dt0 type having an indeterminate growth habit and is adapted to cultivate sesame varieties with the indeterminate growth habit; and if both the product having the band size of 92 bp and the product having the band size of 97 bp are amplified, the germplasm material of the sesame is determined to belong to a hybrid type having the indeterminate growth habit.

5. The method of claim 4, wherein for further determining whether the germplasm material to be identified comprises the Sidt1 gene, the extracted DNA of 1) is used as the template for PCR amplification using the following primer pair:

```
a forward primer Dt1 Primer F represented by SEQ
ID NO. 7:
5'-ATGGCAAAAATGTCATCGGACC-3';
and

a reverse primer Dt1 Primer R represented by SEQ
ID NO. 8:
5'-CTAGCGCCTTCTAGCAGCAGTC-3';
```

the PCR amplified products are sequenced and aligned with the Sidt1 gene, and if the PCR amplified products comprise the Sidt1 gene sequence of SEQ ID NO: 1, the germplasm material to be identified is determined to belong to the determinate florescence phenotype.

* * * * *